(12) United States Patent
Ueki et al.

(10) Patent No.: US 6,580,777 B1
(45) Date of Patent: Jun. 17, 2003

(54) X-RAY CT APPARATUS

(75) Inventors: Hironori Ueki, Kawasaki (JP); Kenichi Okajima, Mitaka (JP)

(73) Assignee: Hitachi Medical Corporation, Tokyo (JP)

( * ) Notice: Subject to any disclaimer, the term of this patent is extended or adjusted under 35 U.S.C. 154(b) by 0 days.

(21) Appl. No.: 09/869,851

(22) PCT Filed: Dec. 10, 1999

(86) PCT No.: PCT/JP99/06945
§ 371 (c)(1),
(2), (4) Date: Jul. 5, 2001

(87) PCT Pub. No.: WO00/40152
PCT Pub. Date: Jul. 13, 2000

(30) Foreign Application Priority Data

Jan. 5, 1999 (JP) ............................................ 11-000292

(51) Int. Cl.⁷ ................................................ A61B 6/02
(52) U.S. Cl. ........................................... 378/17; 378/15
(58) Field of Search ............................. 378/15, 17, 4, 378/8, 196

(56) References Cited

U.S. PATENT DOCUMENTS

| | | | | |
|---|---|---|---|---|
| 4,099,059 A | * | 7/1978 | Distler | 250/445 T |
| 4,716,581 A | * | 12/1987 | Barud | 378/198 |
| 4,741,015 A | * | 4/1988 | Charrier | 378/196 |
| 5,257,183 A | * | 10/1993 | Tam | 364/413.19 |
| 5,357,429 A | * | 10/1994 | Levy | 364/413.15 |
| 5,631,944 A | * | 5/1997 | Kimura et al. | 378/134 |
| 5,799,054 A | * | 8/1998 | Hum et al. | 378/17 |
| 6,075,836 A | * | 6/2000 | Ning | 378/98.12 |
| 6,178,220 B1 | * | 1/2001 | Freundlich et al. | 378/4 |
| 6,324,246 B1 | * | 11/2001 | Ruimi | 378/15 |

* cited by examiner

Primary Examiner—Drew A. Dunn
Assistant Examiner—Irakli Kiknadze
(74) Attorney, Agent, or Firm—Antonelli, Terry, Stout & Kraus, LLP

(57) ABSTRACT

An x-ray CT apparatus of the invention includes: a scanner (4) having an x-ray source (1) for generating radial x-rays emitted to an object (8) and a detector (3) provided to face the x-ray source and acquiring a projection of the object; a rotation controler (102) for rotating the scanner around the object; a gantry-tilt angle controler (104) for changing a tilt angle formed between a surface of rotation of the scanner and a body axis of the object; processing unit (106) for generating a CT image of the object from the projections acquired from a plurality of directions while rotating the scanner and changing the tilt angle; and display unit (107) for displaying a three-dimensional CT image of high picture quality.

11 Claims, 20 Drawing Sheets

$\theta = -\theta o$ $\phi = 0$ (START)

θ = 0

φ = π

$\theta = \theta o$ $\phi = 2\pi$ (END)

X-RAY CT APPARATUS

BACKGROUND OF THE INVENTION

1. Field of the Invention

The present invention relates to an x-ray CT (Computed Tomography) apparatus and, more particularly, to a technique of precisely measuring a three-dimensional (3D) CT image (3D image) of a human body or the like in a large field of view.

2. Description of the Related Prior Arts

As a conventional x-ray CT apparatus, a cone-beam CT apparatus for measuring a 3D CT image of the object is known. The cone-beam CT apparatus is an apparatus for detecting a projection of the object of an x-ray emitted radially (conically) from an x-ray source by a two-dimensional (2D) detector, and reconstructing a 3D CT image of the object. A general cone-beam CT apparatus, as shown in FIG. 22A, rotates a pair of an x-ray tube 1 and a 2D detector 3 around the object 8 and scans the object with the x-ray to obtain a projection. In this case, the orbit of the x-ray source 1 is a circle orbit indicated by a circle 2200. It is, however, known that data necessary for reconstructing a 3D CT image of the object cannot be completely collected with the circle orbit. It causes distortion, artifact, or the like in a reconstructed image, and a problem such that the image quality of an obtained 3D CT image deteriorates arises.

A necessary condition to collect complete data was first taught by a paper of Tuy, "An inversion formula for cone-beam reconstruction", J. Appl. Math., Vol. 43, 1983, pp. 546–552 (Literature 1). Necessary and sufficient conditions were proved by a paper of B. D. Smith, "Image reconstruction from cone-beam projections: Necessary and sufficient conditions and reconstruction methods", IEEE Trans. Med. Imag., Vol. MI-4, 1985, pp. 14 to 25 (Literature 2).

In the following description, the condition disclosed in Literature 1 will be referred to as "Tuy's condition". The Tuy's condition is that "the necessary and sufficient condition to collect complete data is that each of all the planes crossing an object crosses an orbit of an x-ray source at least one point". An example of an x-ray orbit satisfying the Tuy's condition is described in a paper of H. Kudo and T. Saito, "Feasible cone beam scanning methods for exact reconstruction in three-dimensional tomography", J. Opt. Soc. Am. A., Vol. 7, 1990, pp. 2169 to 2183 (Literature 3). In the example of the x-ray orbit described in Literature 3, assuming that the object is a human body, it is difficult to use two circle orbits which perpendicularly cross each other. Preferably, a helical orbit is used.

The inventors of the present invention examined the conventional arts and found the following problems. The scanning method realizing the helical orbit described in Literature 3 can be, as shown in FIG. 21, easily realized by rotating a set of the x-ray source 1 and the detector 3 around the object 8 and, simultaneously, moving the set of the x-ray source 1 and the detector 3 in the direction Z of the rotation axis. However, since the field of view of the detector 3 is also deviated in the direction Z of the rotation axis, a problem such that a shaded common region 601 is limited occurs. In other words, there is a problem such that the 3D region which can be reconstructed is small.

An example of the scanning method for solving the problem that the common region 601 is limited is disclosed in Literature 3. According to the scanning method described in Literature 3, as shown in FIG. 22B, a scan is performed while moving the x-ray source 1 along a helical orbit 2202 on a spherical shell 2201 having a center point O of rotation. By always fixing the center of the view field of the detector 3 at the point O, a large common region is assured. In the following description, the scanning method described in Literature 3 will be referred to as "spherical-helical scan". According to a method of realizing the spherical-helical scan described in Literature 3, as shown in FIG. 22C, the object 8 is rotated around the Z-axis, and the x-ray source 1 is moved on a circular arc 2203 having the point O as a center. In the method described in Literature 3, however, the object 8 has to be rotated. In the case where a human body is assumed as the object 8, a problem such that it is difficult to realize the method occurs. To be specific, due to a centrifugal force accompanying the rotation of the object 8, the object 8 moves during a scan, and a problem such that the picture quality of a 3D CT image deteriorates arises. There is also a problem such that a patient being operated or a patient required to rest in bed cannot be rotated.

SUMMARY OF THE INVENTION

An object of the invention is to provide a technique of collecting complete data necessary to reconstruct an image of the object in a stationary state, further, a technique of acquiring a 3D CT image of a high picture quality, a technique of easily enlarging a common region, and an x-ray CT apparatus capable of realizing improved accuracy of diagnosis of a lung cancer or the like.

The objects and novel features of the invention will become apparent from the description of the specification and the appended drawings.

A representative invention disclosed in the application will be briefly described as follows. As shown in FIG. 6, a scanner (rotary plate) on which a scanning system including an x-ray source 1 and a two-dimensional detector (serving as image acquiring means) 3 is mounted is rotated around an object. Simultaneously, the axis Z' of rotation of the scanner (which coincides with the axis of rotation of the scanning system) is tilted with respect to the body axis direction Z of the object 8. The tilting is performed around the center O of rotation (which coincides with the center of rotation of the scanning system) of the scanner as a center. By carrying out the rotation and tilting simultaneously, a helical scan as shown in FIG. 22B can be realized without rotating the object 8. Since the view field O of the two-dimensional detector 3 is always fixed to the object 8, a common region 601 can be enlarged.

In the configuration of the representative x-ray CT apparatus of the invention, a scanner on which a scanning system is mounted, the scanning system having an x-ray source for generating radial x-rays emitted to an object and image acquiring means provided so as to face the x-ray source and acquiring a projection of the object is rotated around the object by rotating means, a tilt angle formed between a surface of rotation of the scanner and a body axis of the object is changed while rotating the scanner, projections are acquired from a plurality of directions, and a CT image of the object is generated and displayed. The tilting means tilts the surface of rotation of the scanner to change the tilt angle while holding the center of rotation of the scanner almost in a predetermined position. Since the tilt angle is changed so that the upper part of the gantry storing the scanner is moved apart from the head of the object, the upper part of the gantry is moved apart from the field of view of the object and the object does not feel fear. The shortest distance between the rotation center of the scanner and the rotational axis of the tilting means is set to be smaller than spatial resolution of the image acquiring means. Consequently, the spatial resolution of a CT image does not deteriorate.

Further, as functions of the tilting means, various functions exist as follows. The tilt angle is changed by using the straight line almost orthogonal to the axis of center of rotation of the scanner as a central axis. The tilt angle is changed by using the straight line almost orthogonal to the axis of center of rotation of the scanner and the body axis of the object as a central axis. A change amount of the tilt angle with respect to a unit rotation amount of the scanner is held to be constant. A period of rotation of (360°×N) (where, N denotes a natural number) of the scanner by the rotating means is synchronized with a period from start until end of a change of the tilt angle. A period of rotation of (360°×I+α) (where, I denotes a natural number and a denotes an arbitrary angle in a range of 0°<α<360°) of the scanner by the rotating means is synchronized with a period from start until end of a change of the tilt angle. A change in the tilt angle during rotation of the scanner is temporarily stopped. Thus, by combining the functions, various helical scans can be realized. An effect such that collection of complete data necessary to reconstruct the object and enlargement of the common region can be easily achieved is produced.

The scanner can be tilted by tilting the axis Z' of rotation with respect to the object 8 fixed to the floor or by tilting the object 8 with respect to the axis Z' of rotation in a state where the axis Z' of rotation is fixed to the floor. For example, the tilt of the scanner can be realized by tilting a bed (supporting means) 7 for supporting the object while holding the center of rotation of the scanner almost in a predetermined position. When the bed (supporting means) 7 is tilted, the tilt angle is changed by tilting means so that the upper part of the gantry storing the scanner moves apart from the head of the object, so that the object does not feel fear.

By combining a single or a plurality of rotations of the scanner, tilt in one direction, tilt in the reciprocating direction, stop of the tilt during an operation, and the like, various helical scans can be realized. By measuring and recording the rotational angle and tilt angle in each of the scans and using the recorded information at the time of reconstruction, the picture quality of a reconstructed image can be improved.

A representative x-ray CT imaging method of the invention includes: a step of rotating a scanner on which a scanning system is mounted around an object, the scanning system having an x-ray source for generating radial x-rays emitted to the object and image acquiring means (3) provided so as to face the x-ray source; a tilting step of tilting a surface of rotation of the scanner to change a tilt angle formed between the surface of rotation of the scanner and a body axis of the object; an image acquiring step of acquiring projections of the object; an image reproducing step of generating a CT image of the object from the projections acquired from a plurality of directions while rotating the scanner and changing the tilt angle; and a display step of displaying the CT image of the object. A period of rotation of (360°×I+α) (where, I denotes a natural number and α denotes an arbitrary angle in a range of 0°≦α<360°) of the scanner by the rotating means and a period from start until end of a change of the tilt angle are synchronized with each other. The tilting step includes a stopping step in which a change in the tilt angle can be temporarily stopped. The tilt angle can be changed so that an upper part of the gantry housing the scanner is moved away from the head of the object.

Effects obtained by the representative configuration in the invention disclosed in the application will be briefly described as follows. (1) By combining a single or a plurality of rotations of the scanner, tilt in one direction, a change in one direction in the tilt angle formed between the body axis of the object and the surface of rotation of the scanner, a change in the reciprocating directions of positive and negative tilt angles, stop of the tilt during an operation, and the like, various helical scans can be realized. Complete data necessary to reconstruct the object can be collected in a state where the object is stationary. (2) A three-dimensional CT image of a high picture quality can be reconstructed. (3) The common region can be easily enlarged. (4) The improved accuracy of diagnosis of lung cancer and the like can be achieved.

A representative configuration of the invention will be summarized by referring to FIG. 1 as follows. An x-ray CT apparatus includes: a scanner on which a scanning system is mounted, the scanning system having an x-ray source for generating radial x-rays emitted to an object and image acquiring means provided so as to face the x-ray source and acquiring a projection of the object; rotating means for rotating the scanner around the object; and tilting means for changing a tilt angle formed between a surface of rotation of the scanner and a body axis of the object. A three-dimensional CT image of the object is generated from the projections acquired from a plurality of directions while rotating the scanner and changing the tilt angle formed between the surface of rotation of the scanner and the object and displayed. According to the invention, the x-ray CT apparatus can collect complete data necessary to reconstruct an image of the object in a stationary state.

In the following description, a vector of a variable V is indicated by a symbol "$\vec{V}$", and an inner product of vectors $\vec{U}$ and $\vec{Q}$ is expressed as "$\vec{U} \cdot \vec{Q}$".

DESCRIPTION OF THE PREFERRED EMBODIMENTS

Figure 1:
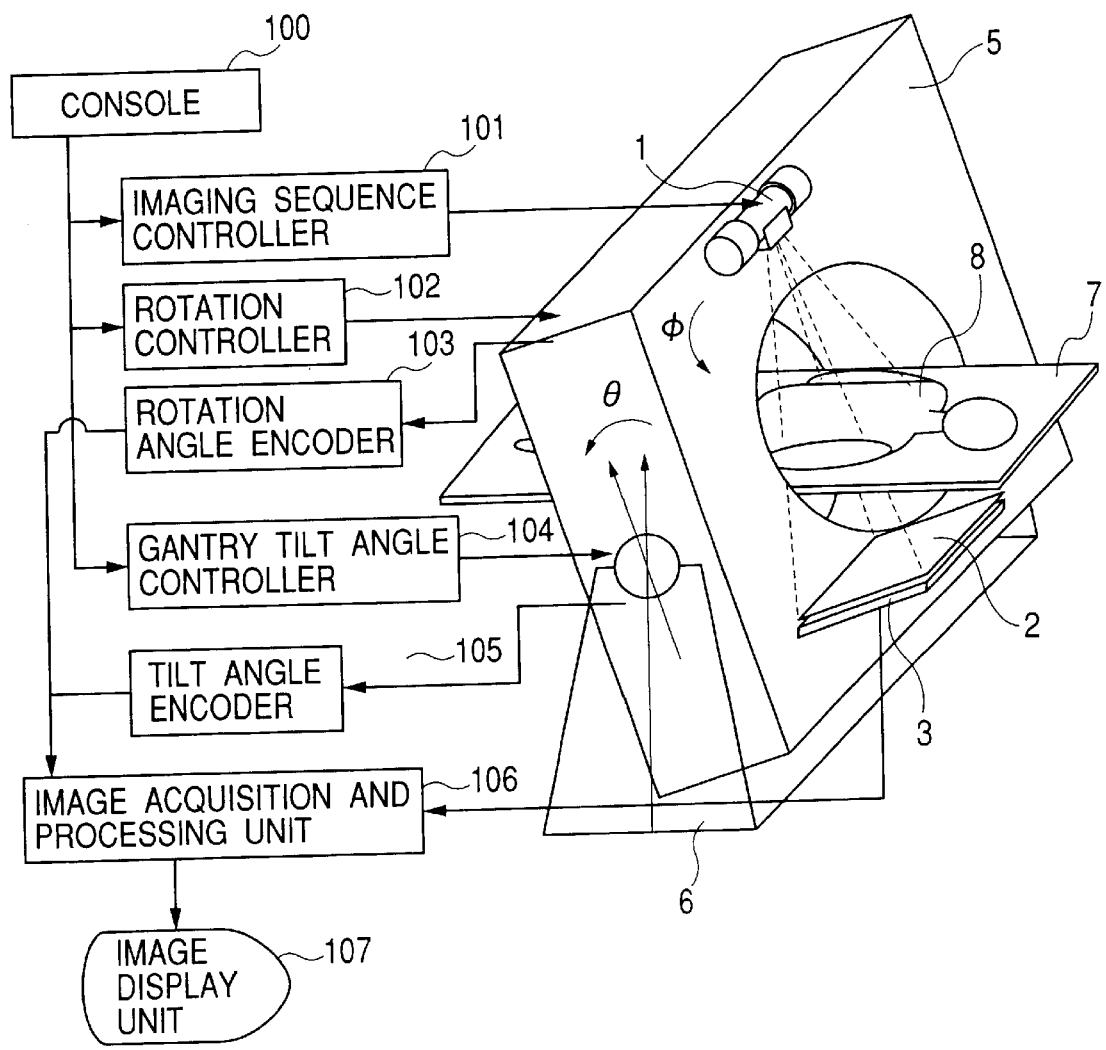
FIG. 1 is a diagram for explaining a schematic configuration of an x-ray CT apparatus according to a first embodiment of the invention.

Embodiments of the invention will be described in detail hereinbelow with reference to the drawings. In all the drawings for explaining the embodiments, components having the same function are designated by the same reference numeral and their description will not be repeated.

FIRST EMBODIMENT (General Configuration)

Figure 2A:
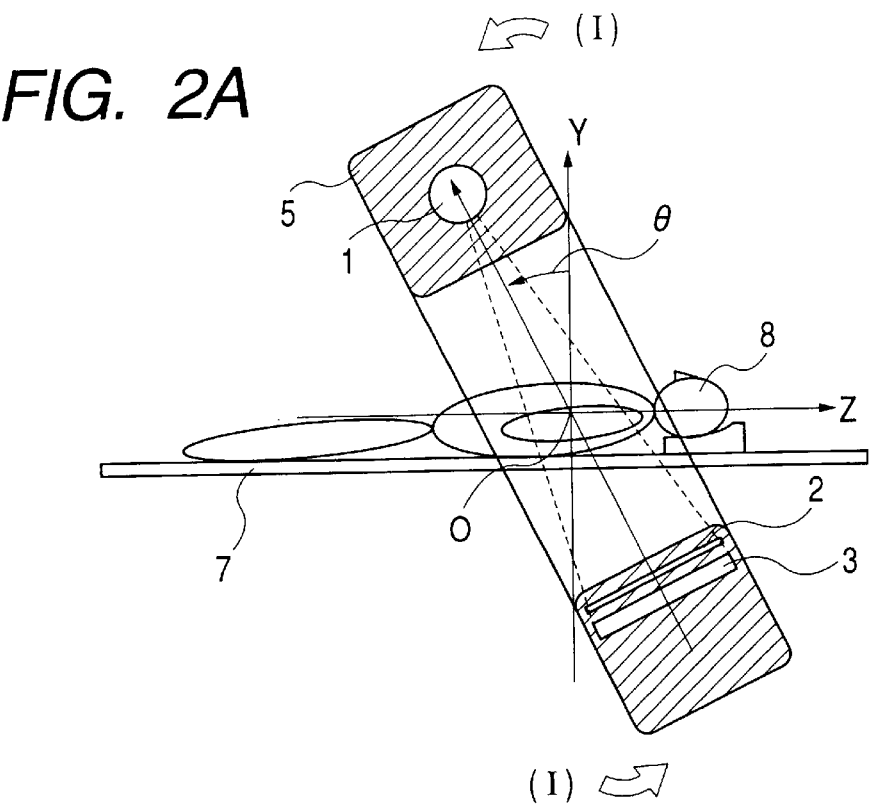
FIGS. 2A and 2B are diagrams each for describing the relation between a rotation angle of a scanning system in the x-ray CT apparatus of the first embodiment and a tilt angle of a gantry.
Figure 2B:
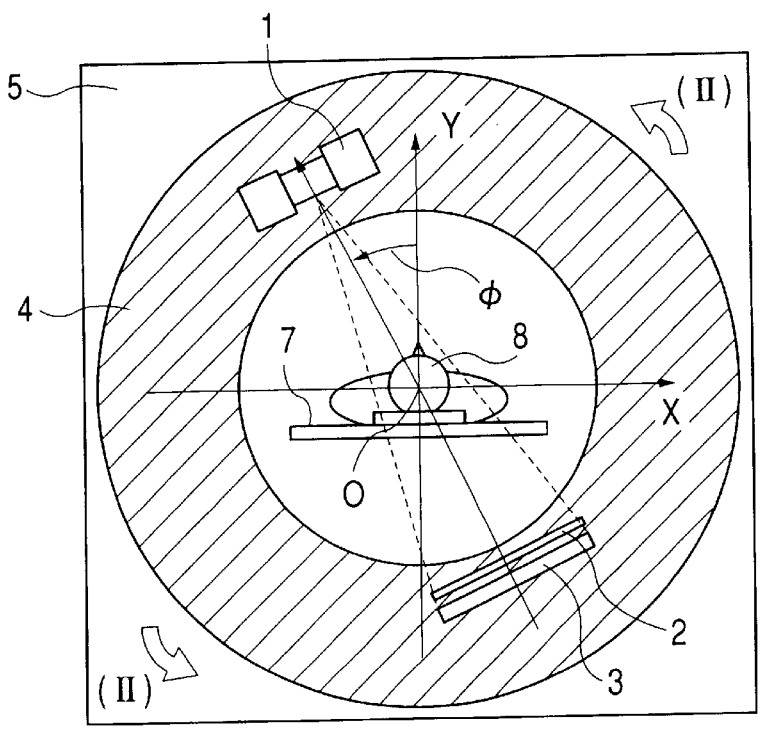

FIG. 1 is a diagram for describing a schematic configuration of an x-ray CT apparatus according to a first embodiment of the invention. FIGS. 2A and 2B are diagrams each for describing the relation between a rotation angle of a scanning system and a tilt angle of a gantry in the x-ray CT apparatus of the first embodiment. Specifically, FIG. 2A is a side view for explaining the tilt angle of the gantry, and FIG. 2B is a front view for explaining the rotation angle of the scanning system. The x-ray CT apparatus according to the first embodiment includes an x-ray tube (x-ray source) 1, an anti-scattering grid 2, a two-dimensional detector 3, a rotary plate (scanner) 4, a gantry 5, a supporting stand 6, a bed 7, a console 100, an imaging sequence controller 101, a rotation controller 102, a rotational angle encoder 103, a gantry-tilt angle controller 104, a tilt angle encoder 105, an image acquisition and processing unit 106, and an image display unit 107. The above devices and mechanisms are known ones. X, Y, and Z shown in FIGS. 2A and 2B represent X axis, Y axis, and Z axis, respectively, having the origin point O as the rotation center O of the rotary plate 4 and are fixed at an object 8. The X axis is fixed in the horizontal direction to the floor. The Y axis is fixed perpendicular to the floor. The Z axis is fixed in the direction of the body axis of the object 8.

The scanning system includes the x-ray tube 1, anti-scanning grid 2, and 2D detector 3 and is fixedly mounted on the rotary plate 4. The rotary plate 4 and the scanning system are housed in the gantry 5. The object 8 is placed on the top face of the bed 7. The scanning system and the rotary plate 4 rotate around the object 8 by using the rotation center (point) O as a center. The gantry 5 is supported by the supporting stand 6. The gantry 5 is tilted by a tilting mechanism (not shown) by using, as a center axis, a straight line parallel to the surface of rotation of the scanning system and passing the center O of rotation, particularly, a straight line (hereinbelow, described as a "tilt central axis") parallel to the floor on which the x-ray CT apparatus is placed.

In the following description, as shown in FIG. 2B, the rotational angle of the x-ray tube 1 with respect to the vertical line shown by the Y axis, that is, the rotational angle of a straight line connecting a focal point of the x-ray tube 1 and the center of the x-ray detector 3 with respect to the vertical line is set as $\phi$. As shown in FIG. 2A, the tilt angle of the gantry from the vertical line, that is, the tilt angle of a straight line connecting the focal point of the x-ray tube 1 and the center of the 2D detector 3 with respect to the vertical line is set as $\theta$. In the first embodiment, in both FIGS. 2A and 2B, the direction of rotation (tilt) indicated by hollow arrows is set as a positive direction. An amount of deviation between the center O of rotation of the scanning system and the tilt central axis (X axis) of the gantry 5 is set to the size of one pixel of the 2D detector 3 or less. The object 8 is irradiated with x-rays emitted from the x-ray tube 1 from various positions ($\phi$ and $\theta$) defined by the rotational angle $\phi$ and the tilt angle $\theta$. The 2D detector 3 disposed so as to face the x-ray tube 1 scans the object 8 with x-rays to acquire a projection, and outputs the acquired projection of the object 8 as an output image to the image acquisition and processing unit 106.

The position with respect to the scanning system of the bed 7 can be adjusted by being moved in the direction of the body axis of the object 8, that is, in the Z axis direction by a not-illustrated bed moving unit. The region of interest (ROI) of the object 8 is set around the center O of rotation. Various 2D detectors 3 are proposed at present. In the first embodiment, a detector constructed by a scintillator, a two-dimensional photo-diode array, and a 2D thin film transistor (TFT) array is used as the 2D detector 3. An example of such a 2D detector is described in a paper of N. Jung et al., "Dynamic X-ray Imaging System based on an Amorphous Silicon Thin-Film Array", Proceedings of SPIE, Vol. 3336, 1998, pp. 396–407 (Literature 4). In the first embodiment, the 2D detector 3 having an x-ray input plane of 200×200 mm, the number of pixels of 1000×1000, and the frame rate of 30 frames per second is used.

The radius D of gyration of the x-ray tube 1 is 720 mm, a distance d between the center O of rotation of the rotary plate 4 and the input plane of the 2D detector 3 is 380 mm, and one side W of the input plane of the 2D detector 3 is 200 mm. The maximum tilt angle of the gantry is $\pm\pi/9$ ($=\pm20°$), and a typical rotation cycle of the scanning system is 4.8 second.

The outline of the components of the x-ray CT apparatus of the first embodiment will now be described. The console 100 sets scan parameters and instructs start of scanning. The imaging sequence controller 101 specifies an imaging sequence for controlling generation of x-rays of the x-ray tube 1 and the scanning operation of the 2D detector 3. The rotation controller 102 controls a rotation sequence of the rotary plate 4. The gantry-tilt angle controller 104 controls a sequence of tilting the gantry 5. The rotational angle encoder 103 measures an angle $\phi$ of rotation of the rotary plate 4 in a scanning mode. The title angle encoder 105 measures the tilt angle $\theta$ of the gantry 5 in the scanning mode. The image acquisition and processing unit 106 acquires an output image (x-ray image) of the 2D detector 3, a rotational angle as a measurement value obtained by the rotational angle encoder 103, and a tilt angle as a measurement value obtained by the tilt angle encoder 105. The image acquisition and processing unit 106 reconstructs a 3D CT image of the object 8 on the basis of the acquired x-ray image, rotational angle, and tilt angle.

The operation of the x-ray CT apparatus according to the first embodiment will now be described. In FIG. 1, x-rays emitted radially as shown by dotted lines from the x-ray tube 1 pass through the object 8, scattered x-rays are removed by the anti-scattering grid 2, and resultant rays are converted to a digital image by the 2D detector 3. The 2D detector 3 can acquire digital images each having 1000×1000 pixels at a rate of 30 frames per second. In a CT scan, in a standard mode, 2×2 pixels are added to thereby obtain one pixel, an image has 500×500 pixels, and a frame rate is 60 frames per second. The CT scan in the standard mode acquires 60 images per second every 1.25°. In a CT scan to obtain images of the object 8 over a 360 degree angular range, 288 images are acquired in 4.8 seconds. The image acquisition and processing unit 106 stores once the output images measured all around the object 8 by the 2D detector 3 together with positional information ($\phi$ and $\theta$) of the x-ray tube 1 into a not-shown memory, reads the output images from the memory, and reconstructs a 3D CT image. The image display unit 107 displays the reconstructed 3D CT image. Alternately, the image acquired by the 2D detector 3 can be displayed on the image display unit 107 in a real-time manner. The x-ray CT apparatus of the first embodiment has a configuration that the center O of rotation of the scanning system coincides with the tilt central axis of the gantry 5. By setting the region of interest (RIO) around the center O of rotation, an image of a wide ROI can be acquired. As a result, a 3D CT image of a relatively large organ such as a lung field can be relatively easily acquired. Thus, the improved accuracy and efficiency of diagnosis can be achieved.

(Scanning Operation)

Figure 3A:
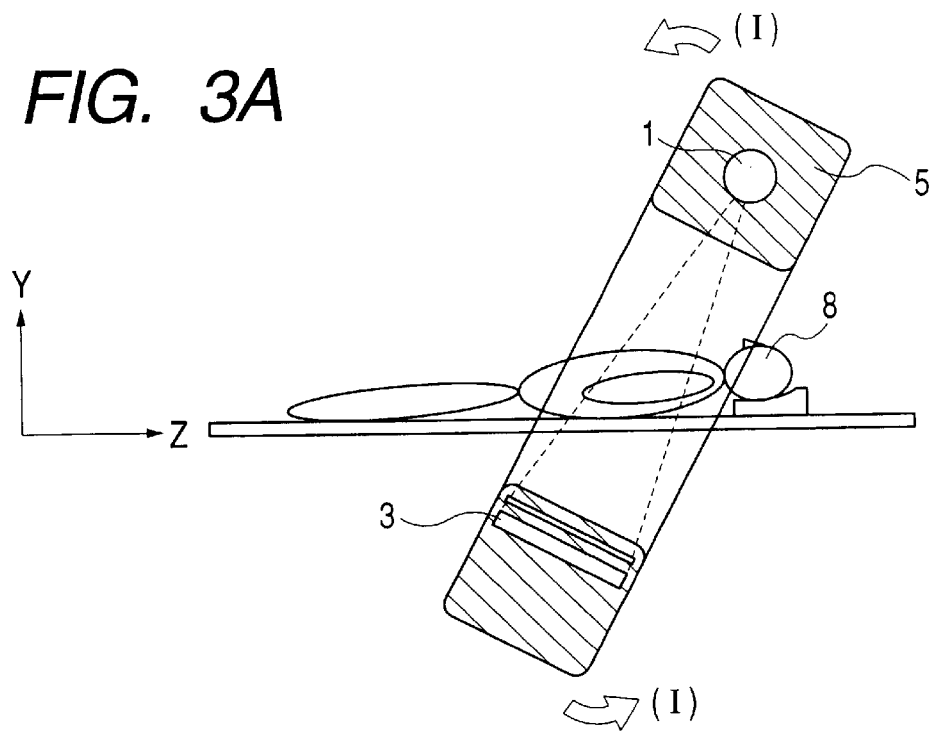
FIGS. 3A and 3B are diagrams each for describing the relation between a rotation angle and a tilt angle at start of scanning in the x-ray CT apparatus of the first embodiment.
Figure 3B:
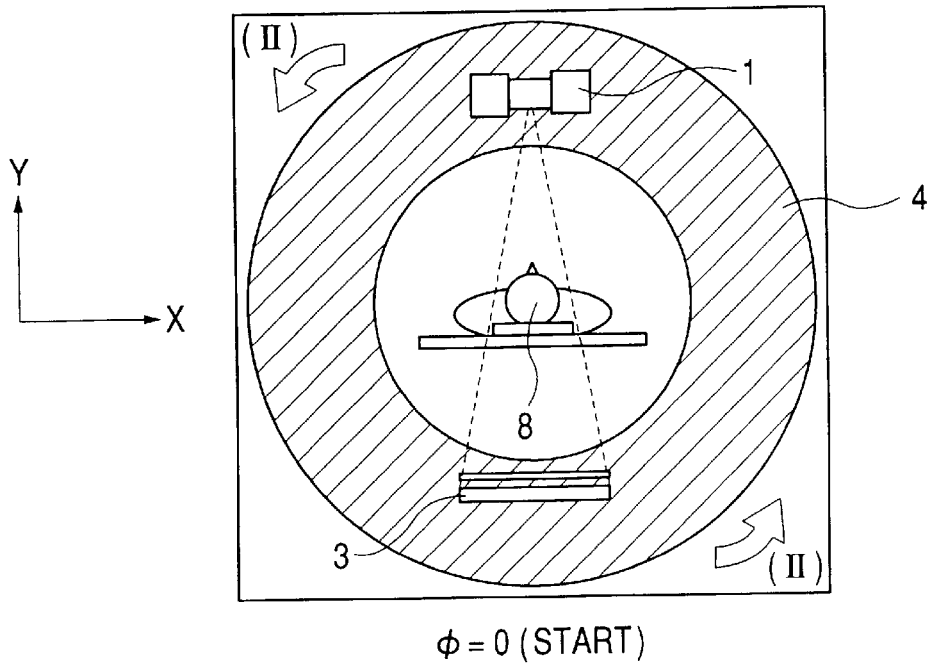
Figure 4A:
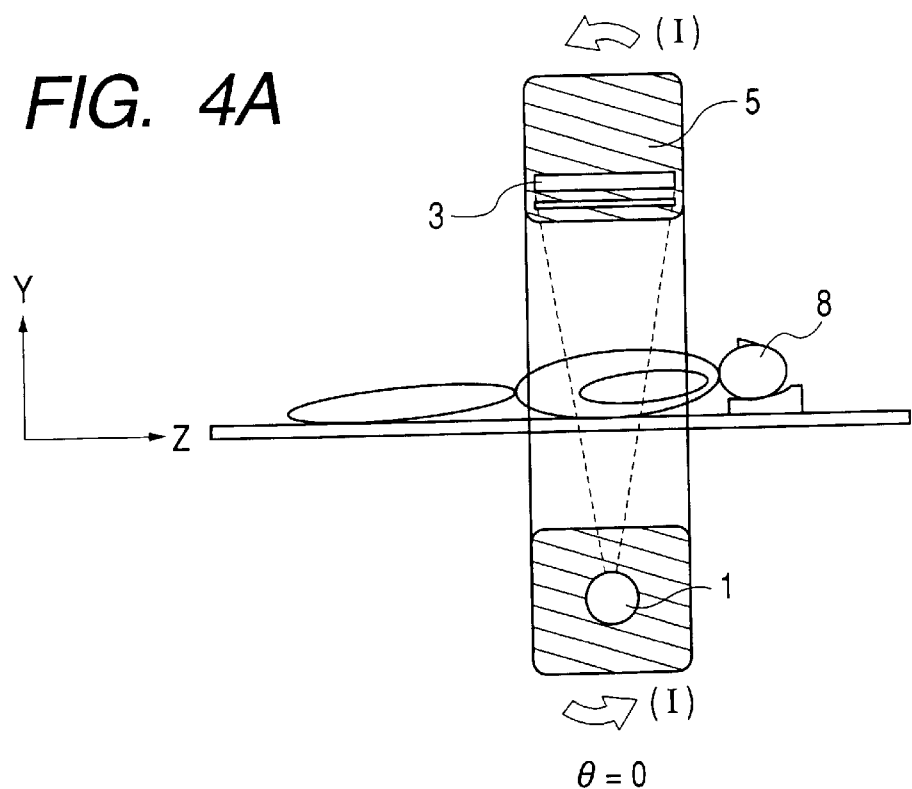
FIGS. 4A and 4B are diagrams each for describing the relation between a rotation angle and a tilt angle when time T/2 has elapsed since the start of scanning in the x-ray CT apparatus of the first embodiment.
Figure 4B:
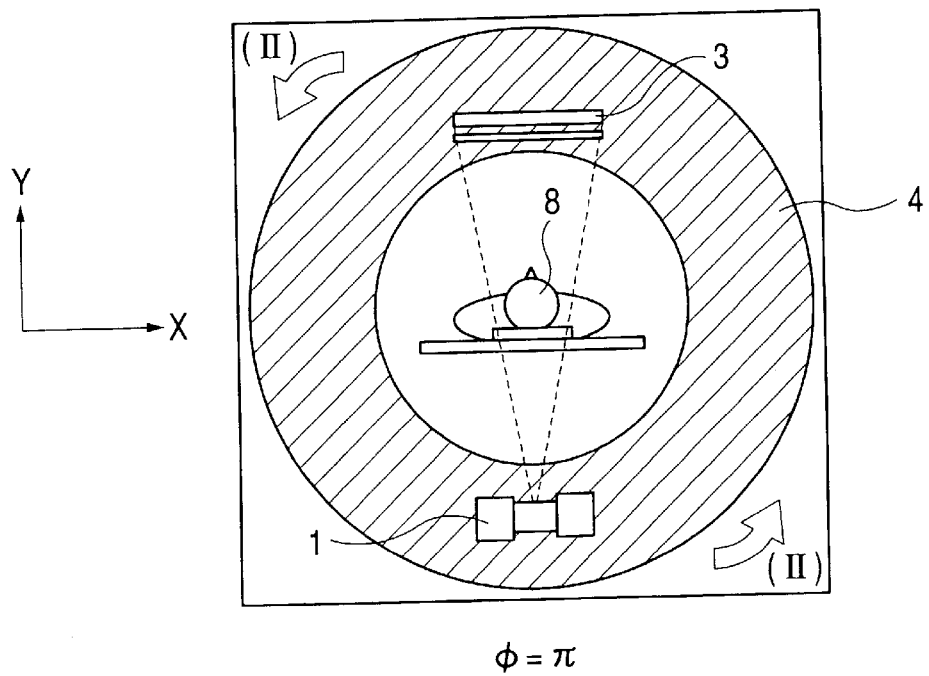
Figure 5A:
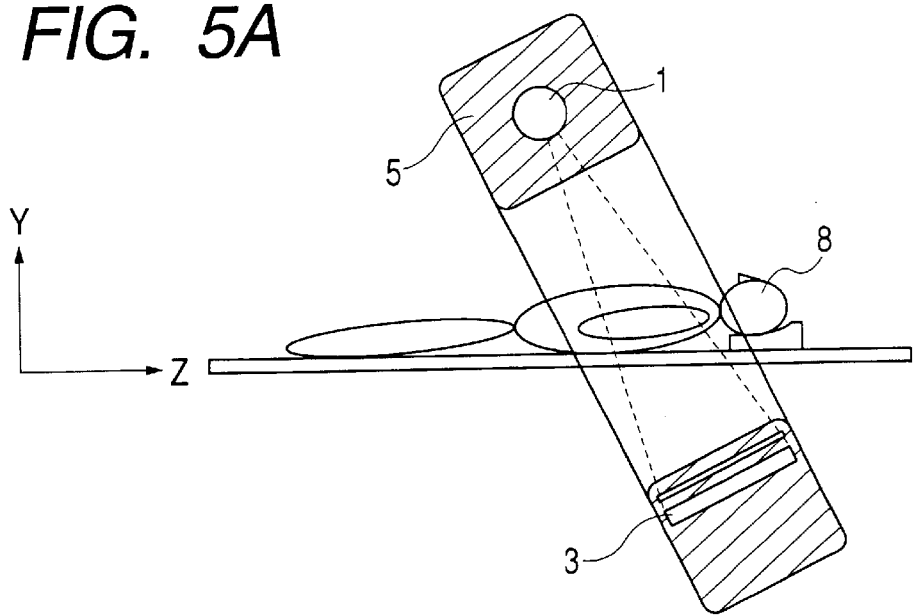
FIGS. 5A and 5B are diagrams each for describing the relation between a rotation angle and a tilt angle when time T has elapsed since the start of scanning in the x-ray CT apparatus of the first embodiment.
Figure 5B:
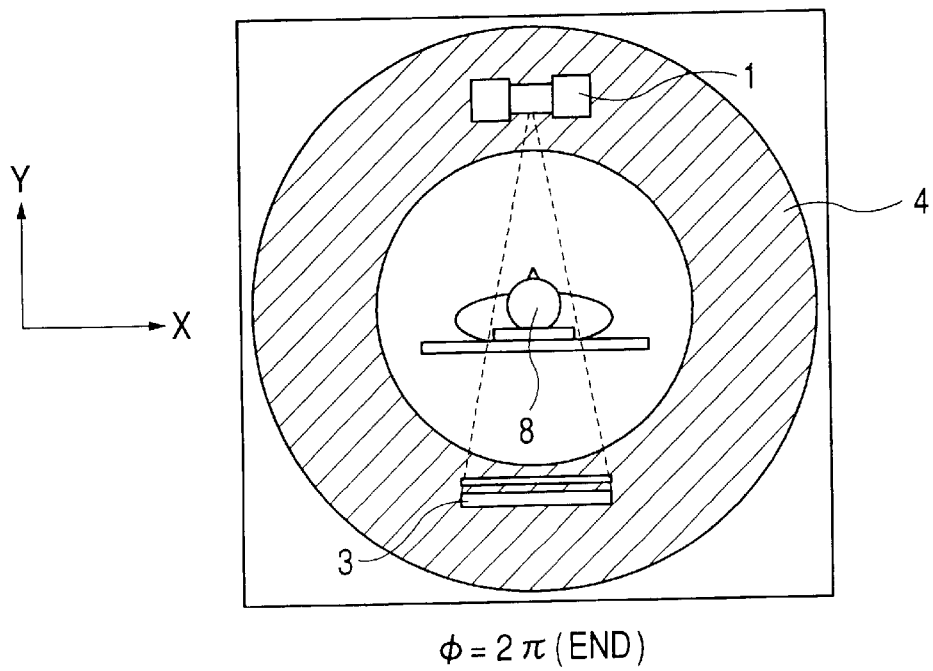

FIGS. 3A, 3B, 4A, 4B, 5A, and 5B are diagrams for explaining an example of the relation between the rotational angle of the scanning system and the tilt angle of the gantry 5 in a period from the start to the end of a scan in the x-ray CT apparatus according to the first embodiment. Specifically, FIGS. 3A and 3B show a state at the start of the scan. FIGS. 4A and 4B show a state after elapse of time only by T/2 since the start of the scan. FIGS. 5A and 5B show a state after elapse of time only by T since the start of the scan. FIGS. 3A, 4A, and 5A are diagrams showing the tilt angle of the gantry with respect to the object in the x-ray CT apparatus of the first embodiment (cross sections of a plane with X=0 in a coordinate system (X, Y, Z) fixed to the object). FIGS. 3B, 4B, and 5B are diagrams each showing the rotational angle of the scanning system with respect to the object in the x-ray CT apparatus of the first embodiment (cross sections of a plane with Z=0 in the coordinate system (X, Y, Z) fixed to the object).

As shown in FIGS. 3A and 3B, the tilt angle $\theta$ of the gantry 5 at the start of a scan is $-\theta 0$, and the rotational angle $\phi$ of the rotary plate 4 is $\phi=\phi 0=0$. In the first embodiment, the initial value $-\theta 0$ of the tilt angle $\theta$ of the gantry 5 can be arbitrarily selected in a range of $\pm 20°$ of the maximum tilt angle by designation of the user from the console 100. A typical initial value $-\theta 0$ is 5.2°. On start of the scan, the rotary plate 4 rotates at a constant angular velocity in the direction indicated by arrows (II) and, simultaneously, the gantry 5 starts to be tilted at a constant angular velocity in the direction indicated by arrows (I). When it is assumed that the cycle of rotation is T (=4.8 seconds), the angular velocity of the rotary plate 4 is 2 $\pi$/T. The angular velocity of the tilt of the gantry 5 is 2×$\theta 0$/T. Consequently, when time elapses only by T/2 since the start of a scan, as shown in FIGS. 4A and 4B, the tilt angle $\theta$ of the gantry 5 becomes zero. The rotational angle $\phi$ of the rotary plate 4 becomes equal to $\pi$. After elapse of time T from the start of the scan, as shown in FIGS. 5A and 5B, the tilt angle $\phi$ of the gantry 5 becomes $\theta 0$, the rotational angle $\phi$ of the rotary plate 4 becomes 2$\pi$, and the scan is finished.

The values of the rotational angle $\phi$ and the tilt angle $\theta$ during the period from the start to the end of m a scan can be expressed by equations 1 using the rotation cycle T of the rotary plate 4 and the elapsed time t from the start of a scan.

The range of the elapsed time t in the equations 1 is 0 to T.

$$\phi=2\pi \times t/T, \theta=-\theta 0+2\times \theta 0\times t/T \quad \text{(Equation 1)}$$

Figure 6:
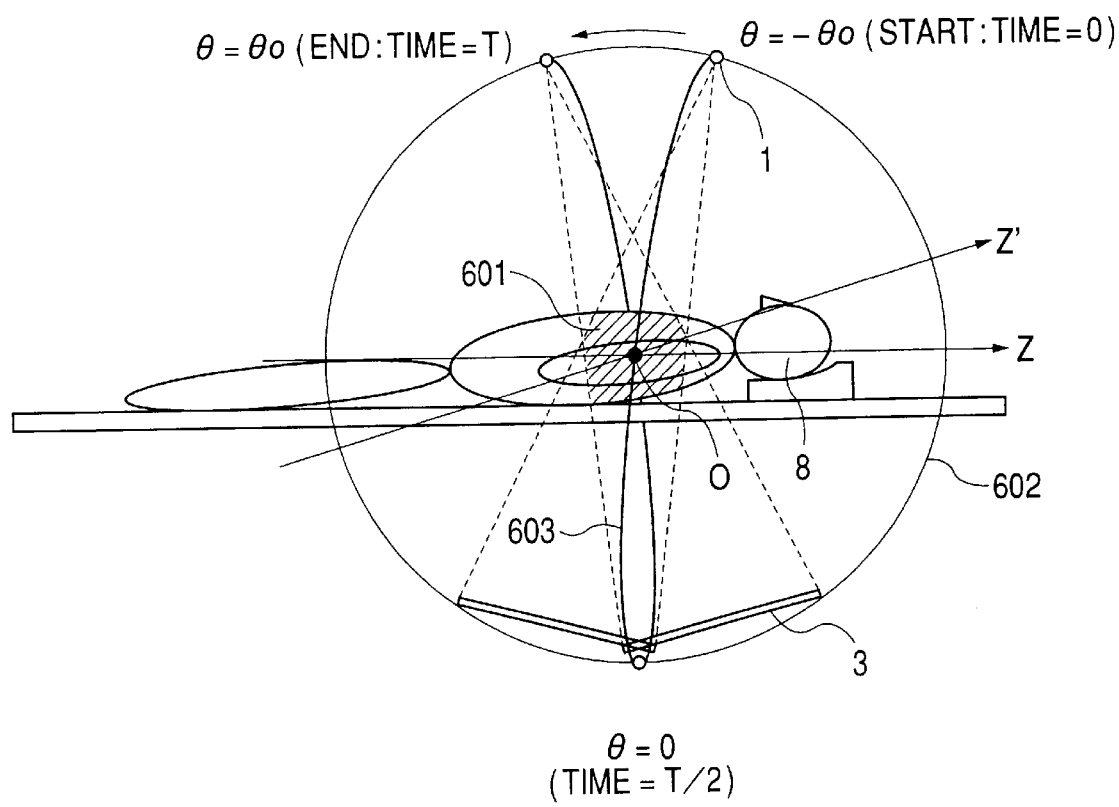
FIG. 6 is a diagram for explaining the positional relation between an x-ray tube position and an object in the x-ray CT apparatus of the first embodiment.

The orbit of the x-ray tube 1 seen from the object 8 is, as shown in FIG. 6, a helical orbit 603 of one rotation along a spherical shell 602 of the radius D of gyration having the center O of rotation as a center. Since the center of the view field of the 2D detector 3 is always fixed to the object 8, an enlarged common region 601 can be realized.

In the first embodiment, the direction of rotation of the rotary plate 4 is set as the $\phi$ direction indicated by the arrows (II). Alternately, it can be set as a $-\phi$ direction opposite to the direction indicated by the arrows (II). Similarly, the direction of the tilt of the gantry 5 may be set as a $-\theta$ direction opposite to the $\theta$ direction indicated by the arrows (I). However, by setting the tilt direction of the gantry 5 to the $\theta$ direction indicated by the arrows (I), as shown in FIG. 3A, the upper part of the gantry 5 can be tilted in the direction apart from the head of the object in a scan, thereby producing an effect such that fear of the object 8 can be lessened.

Figure 7:
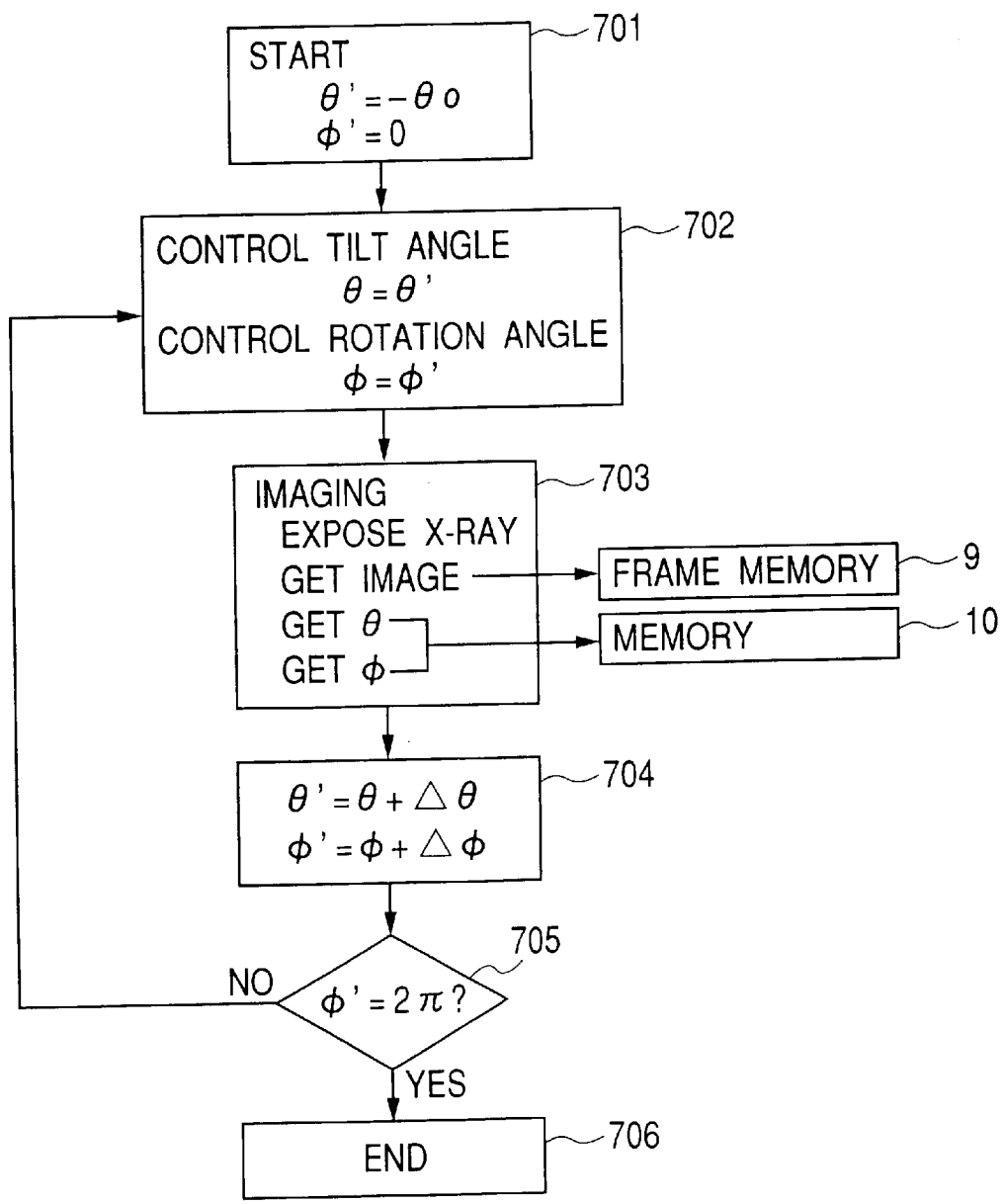
FIG. 7 is a flowchart for explaining a rotation control and the gantry tilt control and a timing of acquiring a projection of the object in the scanning system in a period from the start to the end of a scanning process in the first embodiment.

FIG. 7 is a flowchart for explaining rotation control of the scanning system, control on a tilt of the gantry 5, and scanning timings in a period from the start to the end of a scan in the first embodiment. Based on FIG. 7, a scanning operation in the x-ray CT apparatus of the first embodiment will be described hereinbelow.

step 701: The flowchart of FIG. 7 is started with a measurement start instruction entered from the console 100. First, initial values $\phi'$ and $\theta'$ of the rotational angle of the rotary plate 4 and the tilt angle of the gantry 5, respectively, are set at the start of a scan. The initial set values are that $\phi'=0$ and $\theta'=-\theta 0$.

step 702: Next, the rotating mechanism of the rotary plate 4 and the tilting mechanism of the gantry 5 are controlled so that the rotational angle $\phi$ of the rotary plate 4 and the tilt angle $\theta$ of the gantry 5 become set values $\phi'$ and $\theta'$, respectively.

step 703: On completion of setting of the rotational angle $\phi$ of the rotary plate 4 and the tilt angle $\theta$ of the gantry 5, a scanning operation (x-ray irradiation and image acquisition) is started. An acquired image, that is, a projection of the object obtained by the 2D detector 3 is recorded or stored in the form of digital data into a frame memory 9 of the image acquisition and processing unit 106. In the first embodiment, the values of the tilt angle θ and the rotational angle φ in the scanning operation are measured by the tilt angle encoder 105 and the rotational angle encoder 103, respectively. The measured tilt angle θ and rotational angle φ are recorded or stored in a memory 10 of the image acquisition and processing unit 106. As each of the frame memory 9 and the memory 10, for example, a semiconductor memory device, a magnetic disk device, an optical disk device, or the like is used.

step 704: After completion of recording of the projection of the object at the set values φ' and θ', tilt angle θ, and rotational angle φ, the set value φ' is set to be equal to φ+Δφ, and the set value θ' is set to be equal to θ+Δθ, where Δθ=2π/N and Δθ=2×θ0/N. N denotes the number of images acquired per rotation of the scanning system. A typical value of N is 288.

step 705: When the set value φ' obtained by adding Δφ is equal to 2π, the program advances to the next step and the process is finished (step 706). On the other hand, when the set value φ' obtained by adding Δφ is not equal to 2π, the program returns to step 702, and the processes from step 702 to step 705 are repeated.

In the scanning operation in the x-ray CT apparatus of the first embodiment described by referring to FIG. 7, each of the tilt angle θ and the rotational angle φ is controlled step by step by using a stepping motor or the like provided for a not-illustrated rotating mechanism. In the scanning operation, therefore, the rotary plate 4 and gantry 5 are temporarily in a stationary (stopped) state. To carry out the CT measurement with high accuracy, it is desirable to control the rotary plate 4 and gantry 5 step by step. By controlling the rotation of the rotary plate 4 and gantry 5 step by step, movement of the 2D detector 3 being capturing a projection of the object can be prevented. As a result, a blur in the projection of the object at each rotation angle φ and each tilt angle θ can be prevented, so that improved picture quality of a 3D CT image of the object 8 acquired by reconstruction can be achieved. However, a large inertial force accompanies rotation of the rotary plate 4 and tilt of the gantry 5, so that it is difficult to control the rotary plate 4 and gantry 5 step by step. Consequently, it is also possible to control the rotation of the rotary plate 4 and the tilt of the gantry 5 in a method described hereinbelow.

Figure 8:
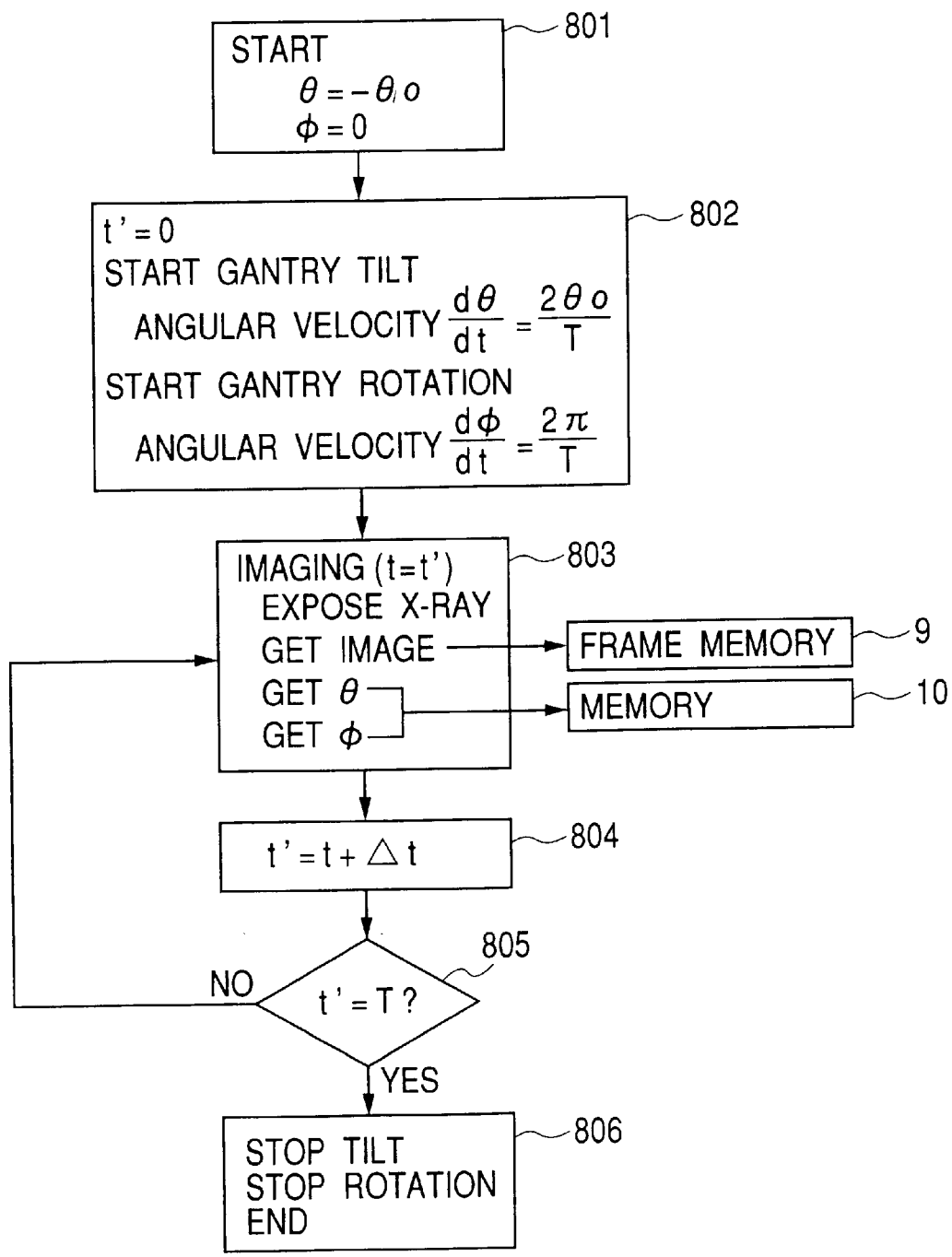
FIG. 8 is a flowchart for explaining another example of rotation control and the gantry tilt control and a timing of acquiring a projection of the object in the scanning system in a period from the start to the end of a scanning process in the first embodiment.

FIG. 8 is a flowchart for explaining another method of rotation control of the scanning system, control on a tilt of the gantry 5, and scanning timings in a period from the start to the end of a scan in the first embodiment. Based on FIG. 8, another scanning operation in the x-ray CT apparatus of the first embodiment will be described hereinbelow.

step 801: The flowchart of FIG. 8 is started with a measurement start instruction entered from the console 100. First, the rotation controller 102 and gantry-tilt angle controller 104 control not-illustrated rotating and tilting mechanisms so that the rotational angle φ of the rotary plate 4 and the tilt angle θ of the gantry 5 are set to initial values 0 and −θ0, respectively, to move the rotary plate 4 and gantry 5.

step 802: Next, the imaging sequence controller 101 sets a set value t' of a scanning operation timing to an initial set value 0. Simultaneously, the gantry-tilt angle controller 104 starts a control of tilting the gantry 5 to the direction θ, and the rotation controller 102 starts a control of rotating the rotary plate 4 to the direction φ. Angular velocities dθ/dt and dφ/dt of the tilt angle θ and the rotational angle φ are equal to 2×θ0/T and 2π/T, respectively, and are constant in the period from the start to the end of the scanning operation.

step 803: When the tilt of the gantry 5 and the rotation of the rotary plate 4 start, simultaneously (at t=t'=0), the imaging sequence controller 101 starts emitting x-rays from the x-ray tube 1. The image acquisition and processing unit 106 collects or acquires a projection of the object outputted from the 2D detector 3. The acquired image is recorded in the form of digital data into the frame memory 9 of the image acquisition and processing unit 106. At this time, the image acquisition and processing unit 106 records the values of the tilt angle φ and the rotational angle φ in the scanning operation which are measured by the tilt angle encoder 105 and the rotational angle encoder 103, respectively, into the memory 10.

step 804: Subsequently, the imaging sequence controller 101 sets a set value t' of an image acquiring timing to t'=t+Δt, where Δt=T/N.

step 805: The imaging sequence controller 101 checks whether the set value t' after Δt was added is equal to T or not. When the set value t' is equal to T, the emission of x-rays is stopped and measurement (acquisition) of a projection of the object is finished. The imaging sequence controller 101 notifies the rotation controller 102 and gantry-tilt angle controller 104 of the end of the scanning operation. The rotation controller 102 notified of the end of the scanning operation stops the rotation of the rotary plate 4, and the gantry-tilt angle controller 104 stops the tilting of the gantry 5 (step 806). On the other hand, when the set value t' obtained by adding Δt is not equal to T, the imaging sequence controller 101 returns to step 803 and repeats the processes from step 803 to step 805.

(Process of Reconstructing 3D CT Image)

Figure 9:
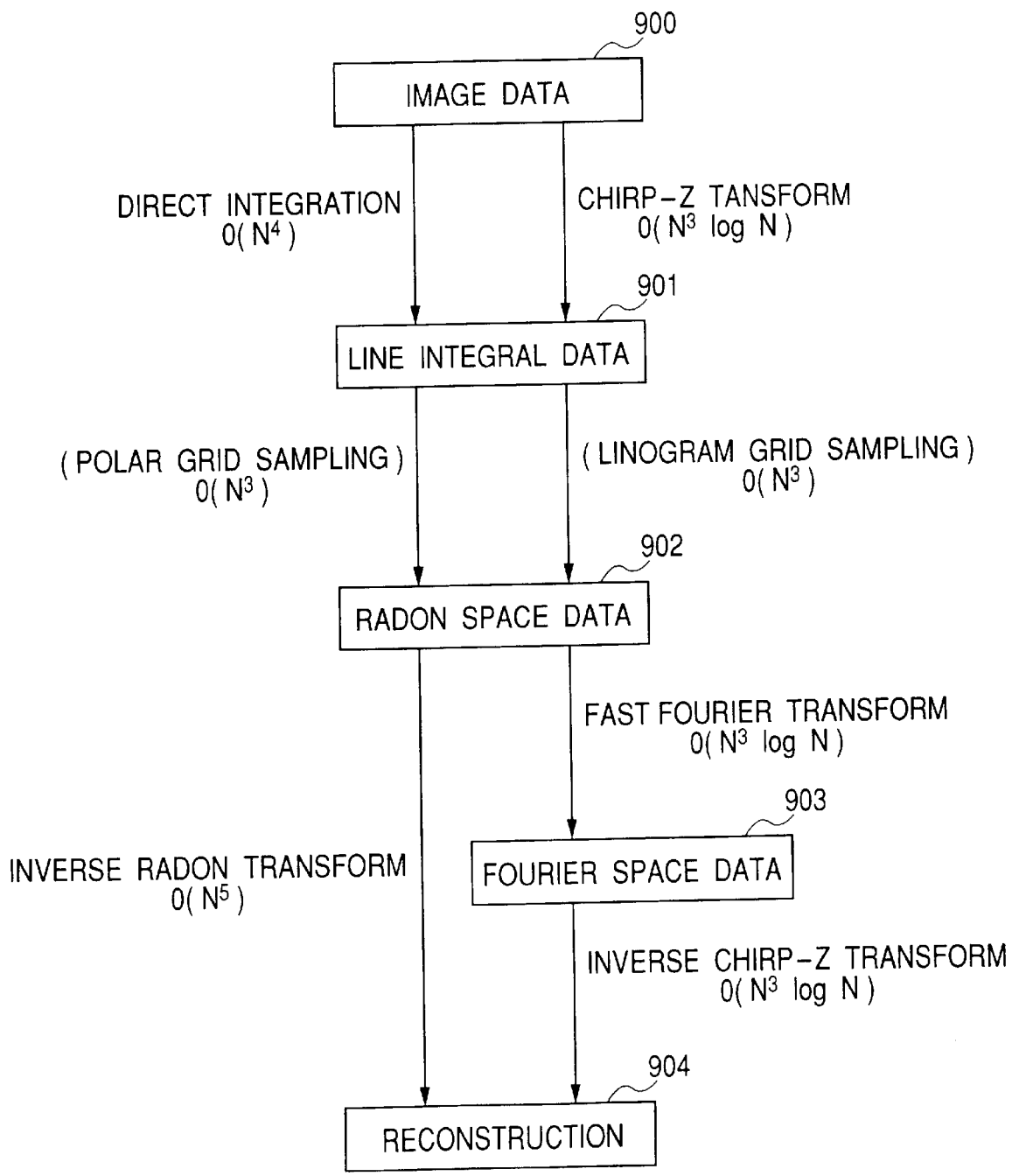
FIG. 9 is a flowchart for explaining a process of reconstructing a 3D CT image from image data collected by the scanning operation in the X-ray CT apparatus of the first embodiment.

FIG. 9 is a flowchart for explaining the procedure of reconstructing a 3D CT image from image data collected by the scan in the x-ray CT apparatus of the first embodiment. Based on FIG. 9, a process of 3D CT image reconstruction executed by the image acquisition and processing unit 106 in the first embodiment will be described hereinbelow. In the following description, since preceding processes such as correction of unevenness of sensitivity of image data read from the frame memory 9, logarithm conversion, and the like are similar to conventional ones, they will not be described. The process of reconstructing a 3D CT image described hereinbelow is executed by the image acquisition and processing unit 106. First, image data 900 stored in the frame memory 9 in the scanning operation is subjected to line integration on an arbitrary straight line in each image and is converted into line integral data 901. As a method of obtaining line integral data, for example, a paper of P. Grangeat, "Mathematical framework of cone-beam 3-D reconstruction via the first derivative of the radon transform", Mathematical Methods in Tomography, New York, Springer, 1991, pp. 66 to 97 (Literature 5) discloses a method of directly executing integration on an image. The method has a problem such that it takes time for calculation since the number of calculation steps is proportional to the fourth power of the number of pixels (hereinbelow, expressed as "$O(N^4)$"). On the other hand, a paper of C. Jacobson and P. E. Danielsson, "3-D reconstruction from cone-beam data in $O(N^3 \log N)$time", Phys. Med., Biol., Vol. 39, 1994, pp. 477 to 491 (Literature 6) discloses a method of performing line integration at high speed at the order of $O(N^3 \log N)$ by using chirp-Z transform. Since the details of calculation of line integration are the same as those of the methods disclosed in Literatures 5 and 6, they will not be described here.

The line integral data 901 is transformed to Radon space data 902. A method of calculating data in an arbitrary position (sample point) in Radon space from the line integral data 901 will be described hereinlater. The Radon space data 902 is collected in a sample point on polar grid or linogram coordinates. Since the polar grid and linogram coordinates are stated in Literatures 5 and 6, they will not be described here. Finally, the Radon space data 902 is transformed to a reconstructed image 904, and the reconstruction is finished. A method of obtaining the reconstructed image 904 from the Radon space data 902 sampled on the polar grid by the inverse Radon transform is disclosed in Literature 5. However, it has a problem that the calculation order is $O(N^5)$ and calculation time is long. Literature 6 discloses a method of obtaining Fourier space data 903 by fast Fourier transform and deriving the reconstructed image 904 by inverse chirp-Z transform. As the calculation order of each of the fast Fourier transform and inverse chirp-Z transform is $O(N^3 \log N)$, reconstruction can be performed at high speed. Since the details of calculation of obtaining the reconstructed image 904 from the Radon space data 902 are the same as those of the methods disclosed in Literatures 5 and 6, they will not be described here.

(Method of Calculating Radon Space Data)

Figure 10:
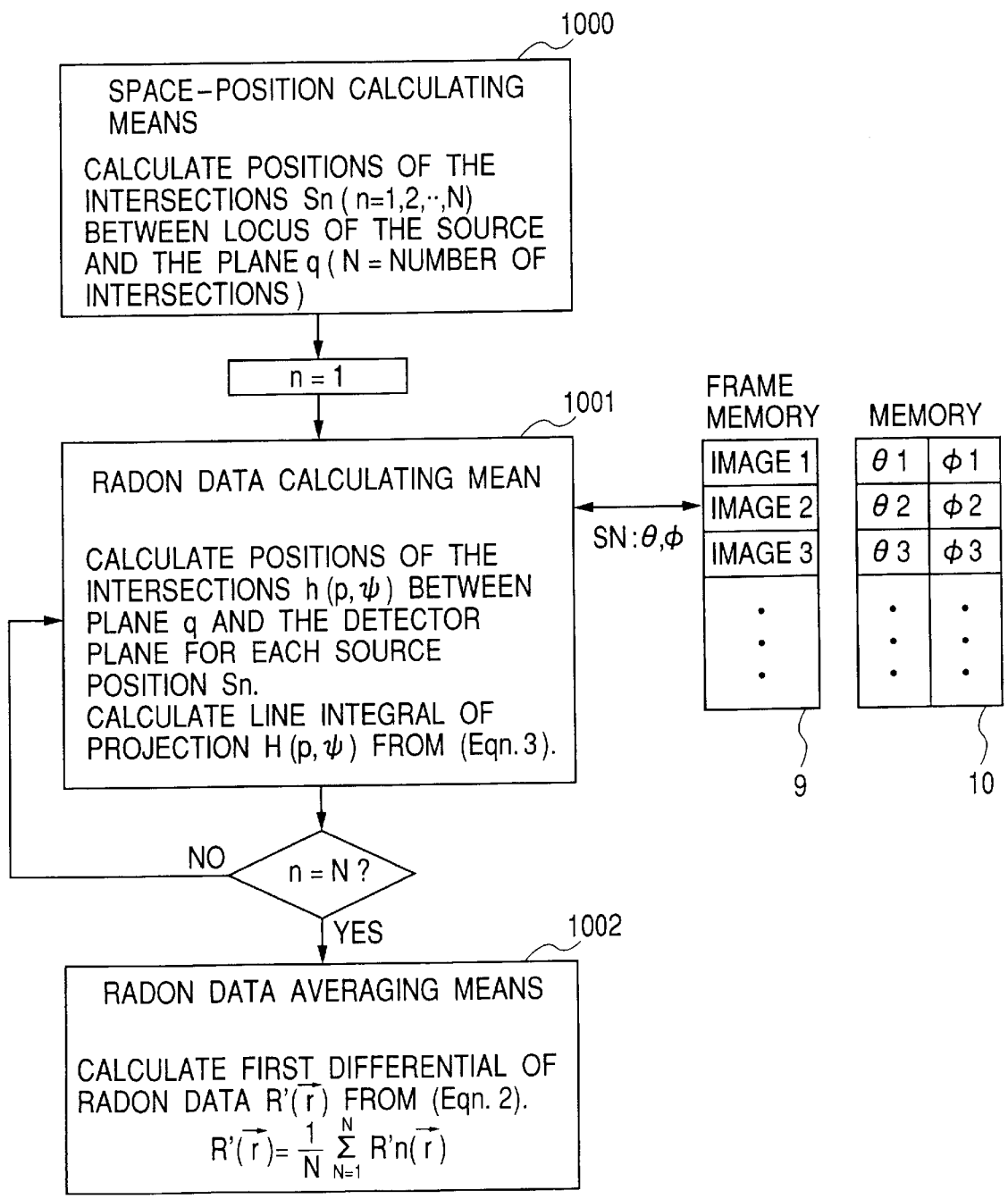
FIG. 10 is a flowchart for explaining a process of calculating Radon space data at an arbitrary sample point $\vec{r}$ from line integral data in the x-ray CT apparatus of the first embodiment.
Figure 11:
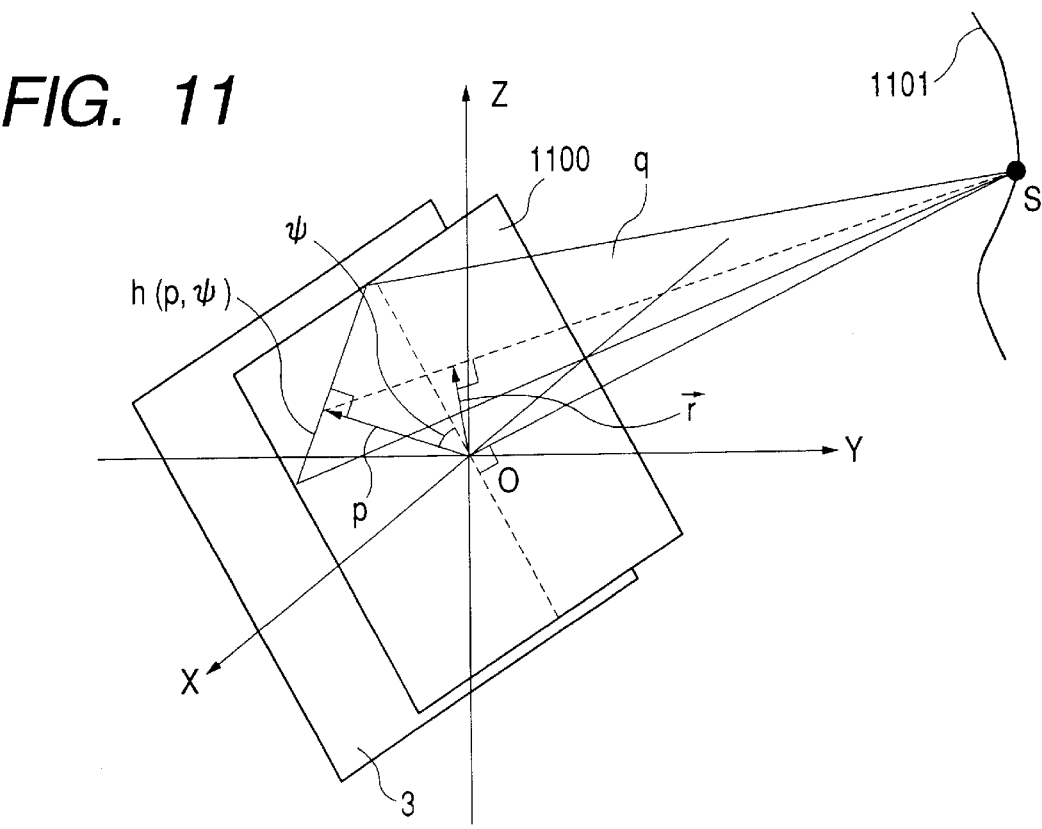
FIG. 11 is a diagram showing the relation between Radon space data at a position $\vec{r}$ and line integral data in the x-ray CT apparatus of the first embodiment.
Figure 12:
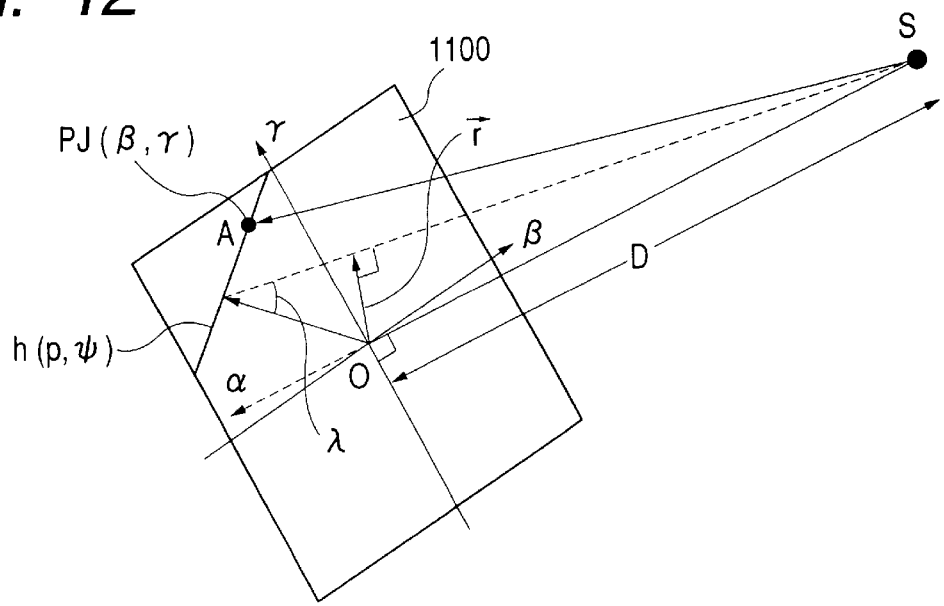
FIG. 12 is a diagram for explaining a coordinate system used to obtain Radon space data in the x-ray CT apparatus of the first embodiment.

FIG. 10 is a flowchart for explaining a process of calculating the Radon space data 902 in an arbitrary sample point $\vec{r}$ (vector) from the line integral data 901. FIG. 11 is a diagram showing the relation between Radon space data in a position $\vec{r}$ and line integral data. FIG. 12 is a diagram for explaining a coordinate system used to obtain Radon space data. In the following, a method of calculating the Radon space data 902 from the line integral data 901 will be described. First, by using FIGS. 11 and 12, parameters used to calculate the Radon space data 902 from the line integral data 901 are defined.

In FIG. 11, the coordinate system (X, Y, Z) is a coordinate system having the center O of rotation of the scanning system as the origin and fixed to the object 8. The Z axis direction corresponds to the direction of the body axis of the object 8. "q" denotes a plane including the position $\vec{r}$ of the arbitrary sample point in the coordinate system (X, Y, Z) and perpendicular to the vector $\vec{r}$. Radon data $R(\vec{r})$ at the position $\vec{r}$ is a surface integral value of a distribution of x-ray attenuation coefficients of the object on the plane q. An imaginary detector 1100 parallel to the 2D detector 3 and crossing the center O of rotation of the scanning system is assumed. An intersection line between the imaginary detector 1100 and x-rays emitted from an x-ray source point S and passed through the plane q is indicated by h. When it is assumed that a perpendicular line from the origin O to the intersection line h is p and an angle formed between a γ axis (which will be described hereinlater) and the perpendicular line p is φ, the intersection line h can be expressed as h(p, φ) on the polar grid (p, φ). The angle formed between the plane p and the imaginary detector 1100 is set as λ.

In FIG. 12, α, β, and γ form a coordinate system having the point O as the origin and fixed to the imaginary detector 1100. Projection data detected in a position A on the imaginary detector is set as PJ(β, γ). Unit vectors in the α, β, and γ directions are indicated as $\vec{\alpha}$, $\vec{\beta}$, and $\vec{\gamma}$, respectively. In this case, Literature 5 proves that Equation 2 is satisfied. H(p, φ) in Equation 2 is a line integral value of projection data PJ(β, γ) on the intersection line h(p, φ) and is expressed by Equation 3. Integration $\int h$ in Equation 3 indicates a line integral on the intersection line h(p, φ). R'($\vec{r}$) indicates a first derivative in the $\vec{r}$ direction of the Radon data R($\vec{r}$). Further, D in Equation 3 denotes a distance between the origin O and the x-ray source point S, and $\overline{SA}$ indicates a distance between the x-ray source point S and the position A on the imaginary detector.

$$\partial H(p, \phi)/\partial p = R'(\vec{r}) \times \sin^2(\lambda) \quad \text{(Equation 2)}$$

$$H(p, \phi) = \int h\{D/\overline{SA}\} \times PJ(p, \gamma)dh \quad \text{(Equation 3)}$$

From Equation 2, by evaluation the integral of the R unit ($\vec{r}$), R ($\vec{r}$) can be obtained. By using Equations 2 and 3, the Radon data R ($\vec{r}$) can be obtained from the line integral data H(p, φ).

A process of calculating Radon space data from line integral data will now be described by referring to FIG. 10. First, space-position calculating means 1000 calculates the intersections S between the plane q including the sample point $\vec{r}$ and perpendicular to the vector $\vec{r}$ and an orbit 1101 of the x-ray tube (x-ray source). An orbit $\vec{S}$ (t) of the x-ray source is expressed by Equation 4. The tile angle θ and the rotational angle φ in Equation 4 are functions of t as shown in Equation 1 and determined according to a scan method. Other examples of the tilt angle θ and the rotation angle φ are expressed by Equations 8 to 16 which will be described later.

$$\vec{S}(t) = (-D \times \cos\theta \times \sin\phi, D \times \cos\theta \times \cos\phi, D \times \sin\theta) \quad \text{(Equation 4)}$$

The intersection S between the plane q and the orbit 1001 of the x-ray tube 1 is obtained by Equation 5.

$$\vec{r} \cdot \vec{S}(t) = |\vec{r}|^2 \quad \text{(Equation 5)}$$

Equation 5 can be easily calculated by numerical calculation such as Newton's method or bisection method. Generally, Equation 5 has a plurality of solutions, so that intersections are indicated by Sn (n=1 to N).

Radon data calculating means 1001 searches the memory 10 for an image obtained at the x-ray tube position Sn and reads image data from the frame memory 9. Further, a line integral value H(p, φ) on the straight line h(p, φ) on the image data is calculated, and a first derivative R'n ($\vec{r}$) of Radon data is calculated by using Equation 2. The values (p, φ) are expressed by Equations 6 and 7.

$$p = D \times |\vec{r}|/\sqrt{(D^2 - |\vec{r}|^2)} \quad \text{(Equation 6)}$$

$$\theta = \tan^{-1}\{(-\vec{r} \cdot \vec{\beta})/(\vec{r} \cdot \vec{\gamma})\} \quad \text{(Equation 7)}$$

Finally, Radon data averaging means 1002 calculates an average of first derivatives R'n ($\vec{r}$) (n=1 to N) of Radon data, and uses the average as a first derivative R' ($\vec{r}$) of Radon data in the position $\vec{r}$. By executing the process on all sampling points $\vec{r}$, all the data in the Radon space can be calculated.

(Other Examples of Orbit of X-ray Tube 1)

Figure 13A:
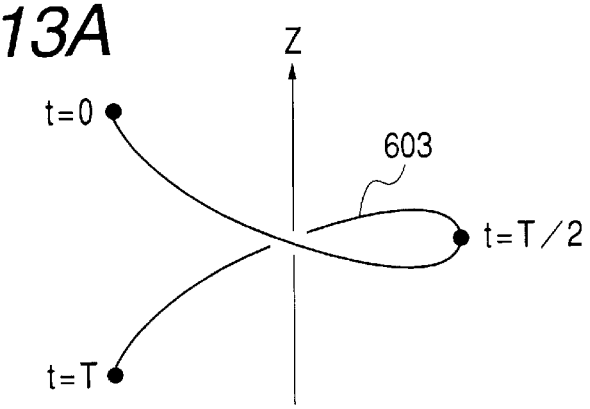
FIGS. 13A, 13B, and 13C are diagrams for explaining another example of the scanning method in the x-ray CT apparatus of the first embodiment.
Figure 13B:
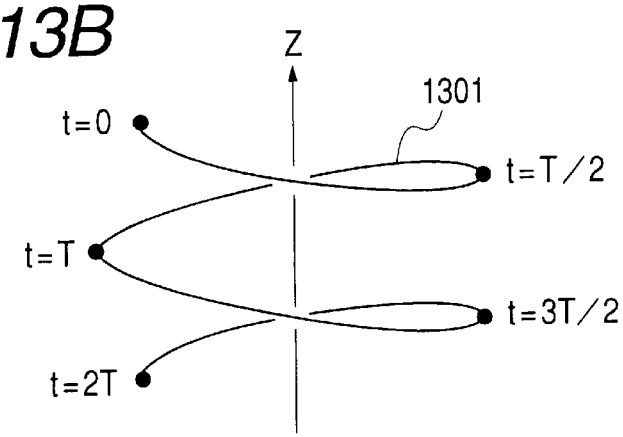

FIGS. 13A, 13B, 13C, 14A, and 14B are diagrams for explaining other examples of the scanning method in the x-ray CT apparatus of the first embodiment. Each of FIGS. 13A, 13B, 13C, 14A, and 14B shows only the relation between the Z axis, the x-ray tube 1, and time t for simplicity of explanation. Specifically, FIG. 13A shows the orbit 603 of the x-ray tube 1 shown in FIG. 6. As obviously understood from FIG. 13A, the another orbit of the x-ray tube 1 also extends along the spherical face 602.

In the examples of the scan shown in FIGS. 3A, 3B, 4A, 4B, 5A, and 5B, the orbit of the x-ray tube 1 is the helical orbit 603 of one rotation as shown in FIG. 13A. The scanning method is not limited to the example. Alternatively, for example, an orbit 1301 of two rotations shown in FIG.

13B may be used. The orbit 1301 can be realized by synchronizing the two rotations of the scanning system corresponding to t (=0 to T) and t (=T to 2×T) and a tilt of the gantry 5 in the range where the tilt angle θ=−θ to θ. The control method is expressed by Equation 8. Time t elapsed from the start of measurement in Equation 8 is equal to (0 to 2×T).

$$\phi=2\pi\times t/T,\ \theta=-\theta 0+\theta 0\times t/T \quad \text{(Equation 8)}$$

In a similar manner, arbitrary one or more rotations (for example, 1.2 rotations or 2.5 rotations) of the scanning system and the tilt of the gantry 5 can be synchronized.

As described above, by continuously carrying out the rotation of the scanning system and the tilt of the gantry 5, continuity of projections can be maintained. Consequently, artifact in a reconstructed image which is caused by a positional deviation or the like can be largely reduced, and the picture quality of a 3D CT image can be improved. The plurality of rotations of the scanning system and reciprocating motion of the tilt of the gantry 5 can be also combined.

Figure 13C:
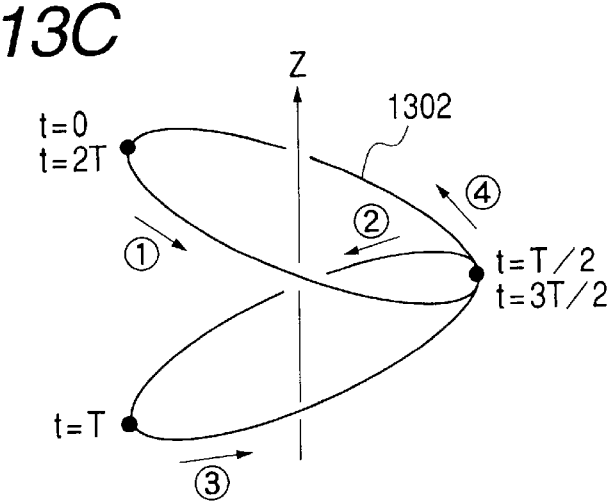
Figure 14A:
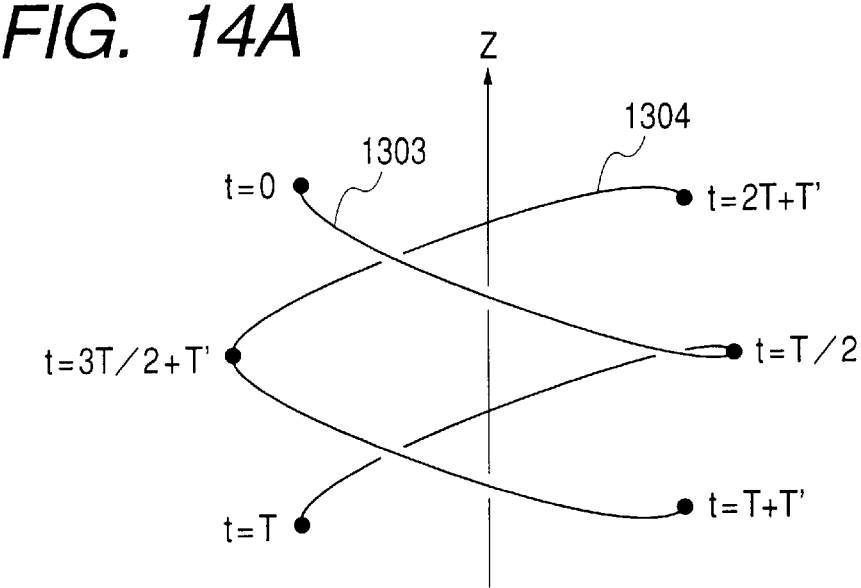
FIGS. 14A and 14B are diagrams for explaining another example of the scanning method in the x-ray CT apparatus of the first embodiment.
Figure 14B:
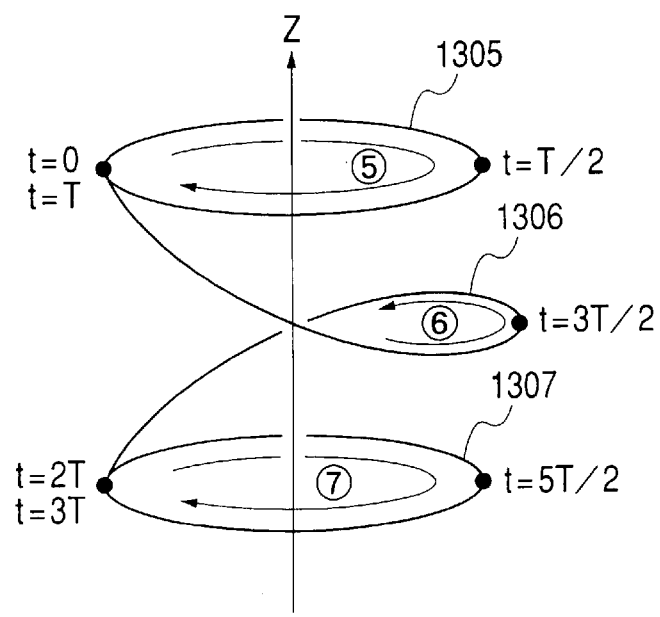
Figure 15:
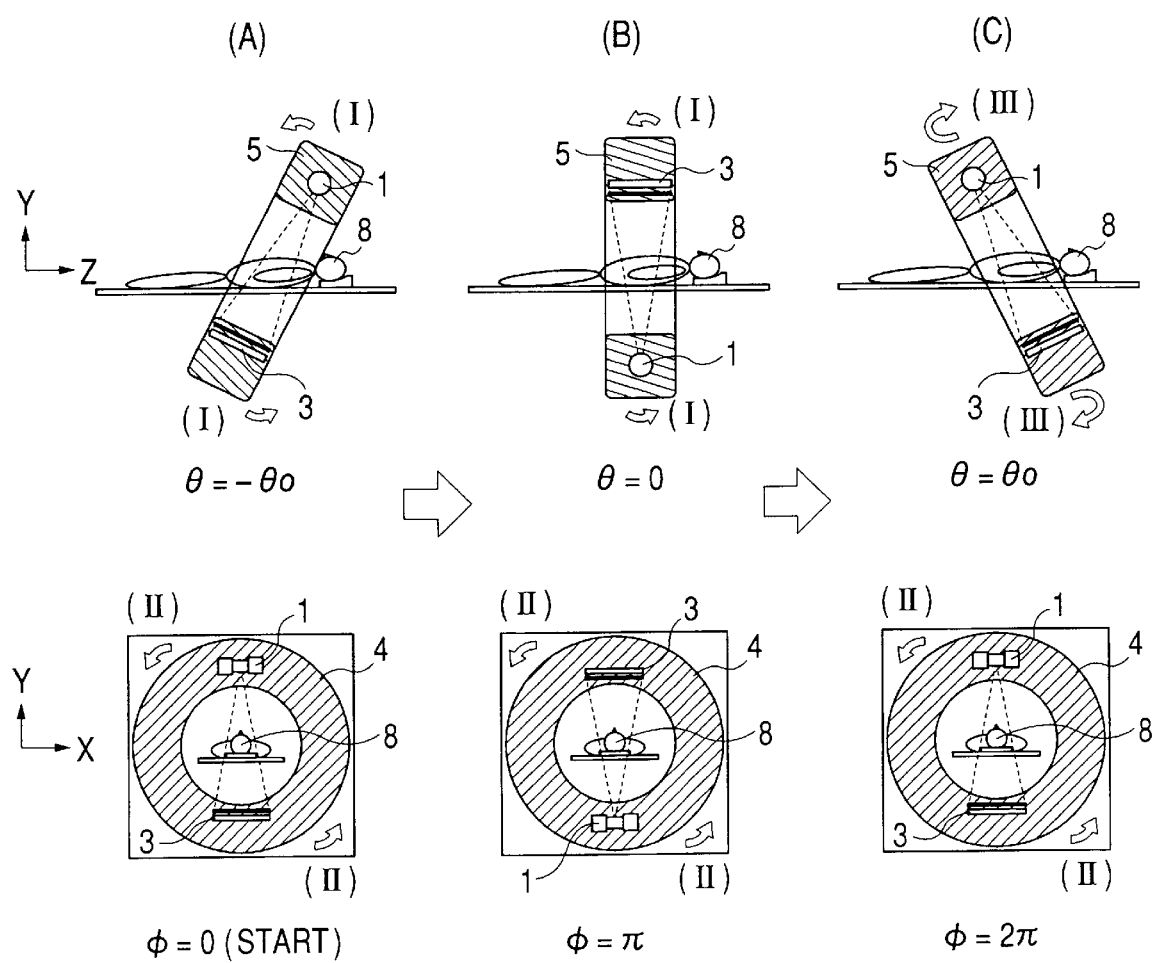
FIGS. 15 and 16 are diagrams each describing the relation between the rotation angle and the tilt angle in the case where a plurality of rotations of the scanning system and reciprocating motion of the gantry are combined.
Figure 16:
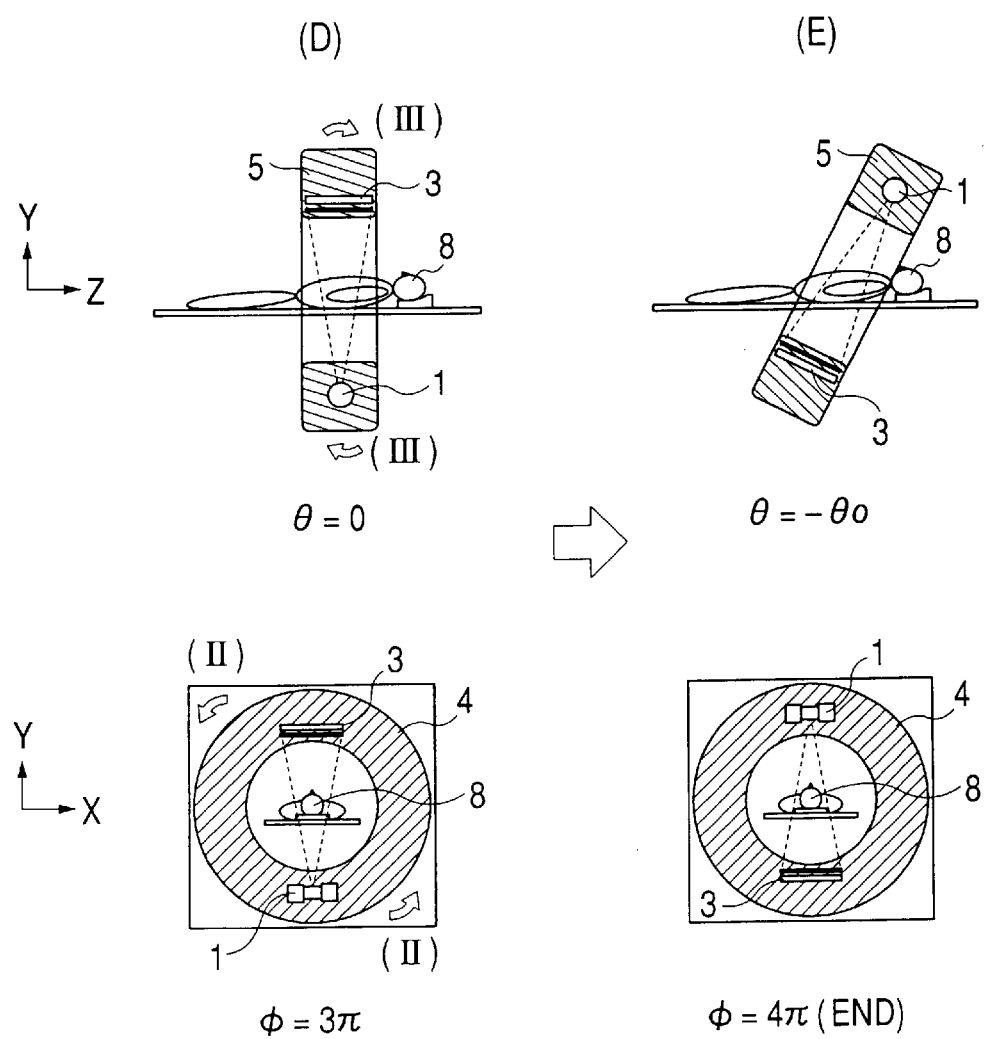

FIGS. 15 and 16 are diagrams each for explaining the relation between the rotational angle and the tilt angle in the case where the plurality of rotations of the scanning system and the reciprocating motion of the tilt of the gantry 5 are combined. In FIGS. 15 and 16, the rotational angle φ is shown by a cross section of a plane of X=0 in a coordinate system (X, Y, Z) fixed to the object, and the tilt angle φ is shown by a cross section of a plane of Z=0 in the coordinate system (X, Y, Z) fixed to the object. In FIG. 15, from a state where φ=0 (A) to a state where φ=2π, the scanning method is the same as that of the example shown in FIGS. 3A, 3B, 4A, 4B, 5A, and 5B. According to the scanning method shown in FIGS. 15 and 16, at the time (C) when φ=2π, the rotary plate 4 continues rotating in the φ direction (arrow (II)). After the state where φ=3π (D), the scan is finished at time point (E) when φ becomes 4π. At time point (C) when φ=2θ, the gantry 5 changes its tilt direction to the −θ direction (direction of the arrow (III)). After the state where θ=0 (D), the scan is finished at time point (E) when θ becomes −θ0. The control method in this case is expressed by Equations 9 and 10 and the orbit of the x-ray tube 1 draws a closed curve as shown in FIG. 13C. Reference numerals 1̂ to 4̂ shown in FIG. 13C denote the order of the orbit of the x-ray tube 1, and the x-ray tube 1 draws the orbit in the direction shown by 1̂ in the period where t=0 to T/2. In the period where t=T/2 to T, the x-ray tube 1 draws the orbit in the direction shown by 2̂. In the period where t=T to 3T/2, the x-ray tube 1 draws the orbit in the direction shown by 3̂. In the period where t=3T/2 to 2T, the x-ray tube 1 draws the orbit in the direction shown by 4̂. The period of t in Equation 9 is 0 to T, and the period of t in Equation 10 is T to 2×T.

$$\phi=2\pi\times t/T,\ \theta=-\theta 0+2\times\theta 0\times t/T \quad \text{(Equation 9)}$$

$$\phi=2\pi\times t/T,\ \theta=\theta 0-2\times\theta 0\times(t-T)/T \quad \text{(Equation 10)}$$

By providing a period in which no scanning process is performed in some midpoint, the orbit of the x-ray source 1 can be made discontinued. For example, in the example of the orbit shown in FIG. 14, two helical orbits 1303 and 1304 in which t=0 to T and t=T+T' to 2T+T' form a double helix. The control method is expressed by Equations 11 to 13. The period of t in Equation 11 is 0 to T, the period of t in Equation 12 is T to T+T', and the period of t in Equation 13 is T+T' to 2×T+T'.

$$\phi=2\pi\times t/T,\ \theta=-\theta 0+2\times\theta 0\times t/T \quad \text{(Equation 11)}$$

$$\phi=2\pi+\pi\times(t-T)/T',\ \theta=\theta 0 \quad \text{(Equation 12)}$$

$$\phi=3\pi-2\pi\times(t-T-T')/T,\ \theta=\theta 0-2\times\theta 0\times(t-T-T')/T \quad \text{(Equation 13)}$$

In the period where t=T to T+T', the scanning operation (irradiation of x-rays and detection of a projection of the object) is stopped. An arbitrary period is valid as T'. In order to reduce the influence of movement of the object, T' has to be set as short as possible (for example, T/4). In the period where t=T+T' to 2×T+T', the rotating direction of the rotary plate 4 is inverted (to the −φ direction).

Further, in a certain period, the tilting of the gantry 5 can be also stopped. For example, in the example of the orbit shown in FIG. 14B, a helical orbit 1306 is sandwiched by two circular orbits 1305 and 1307. The control method at this time is expressed by Equations 14 to 16. The period of t in Equation 14 is 0 to T, that in Equation 15 is T to 2×T, and that in Equation 16 is 2×T to 3×T.

$$\phi=2\pi\times t/T,\ \theta=-\theta 0 \quad \text{(Equation 14)}$$

$$\phi=2\pi-2\pi\times(t-T)/T,\ \theta=-\theta 0+2\times\theta 0\times(t-T)/T \quad \text{(Equation 15)}$$

$$\phi=2\pi\times(t-2\times T)/T,\ \theta=\theta 0 \quad \text{(Equation 16)}$$

The orbit 1305 is drawn in the direction indicated by the arrow 5̂ in the period where t=0 to T. In the period where t=T to 2T, the orbit 1306 is drawn in the direction indicated by the arrow 6̂. In the period where t=2T to 3T, the orbit 1307 is drawn in the direction shown by the arrow 7̂. The orbits 1305 and 1307 are formed by fixing the tilt angle θ of the gantry 5 to −θ0 and θ0 in the periods where t=0 to T and t=2×T to 3×T, respectively.

Although some examples of the scanning method are shown in FIGS. 13A, 13B, 13C, 14A, and 14B, the scanning method is not limited to the above examples. By freely combining rotation of the scanning system (that is, a scanner), tilting of the gantry 5, stop of the scan in a part of the period, stop of rotation of the scanning system or stop of tilting of the gantry 5 in a part of the period, and the like, various scans can be executed.

As described above, in the x-ray CT apparatus of the first embodiment, the gantry 5 housing the scanning system fixed to the rotary plate 4 can be tilted on the supporting stand 6. At the time of a scan, while the scanning system is rotated, the gantry 5 is tilted, thereby enabling the orbit of the x-ray source to be formed helical around the object 8. That is, complete data satisfying the Tuy's condition can be measured. Since accurate reconstruction of a 3D CT image can be reconstructed, a 3D CT image in which occurrence of image distortion and artifact is prevented can be reconstructed. Since the center of the view field of the 2D detector 3 is always fixed to the center O of rotation of the scanning system, reduction in the scan area in association with the movement of the x-ray tube 1 can be prevented, and the improved accuracy of diagnosis of a lung cancer and the like can be achieved. Since the helical scan can be realized only by tilting the gantry 5, complete data can be collected without moving the object 8 as in the conventional techniques. Thus, a positional deviation accompanying the rotation of the object 8 does not occur, so that deterioration in picture quality of a 3D CT image can be prevented.

SECOND EMBODIMENT

Figure 17:
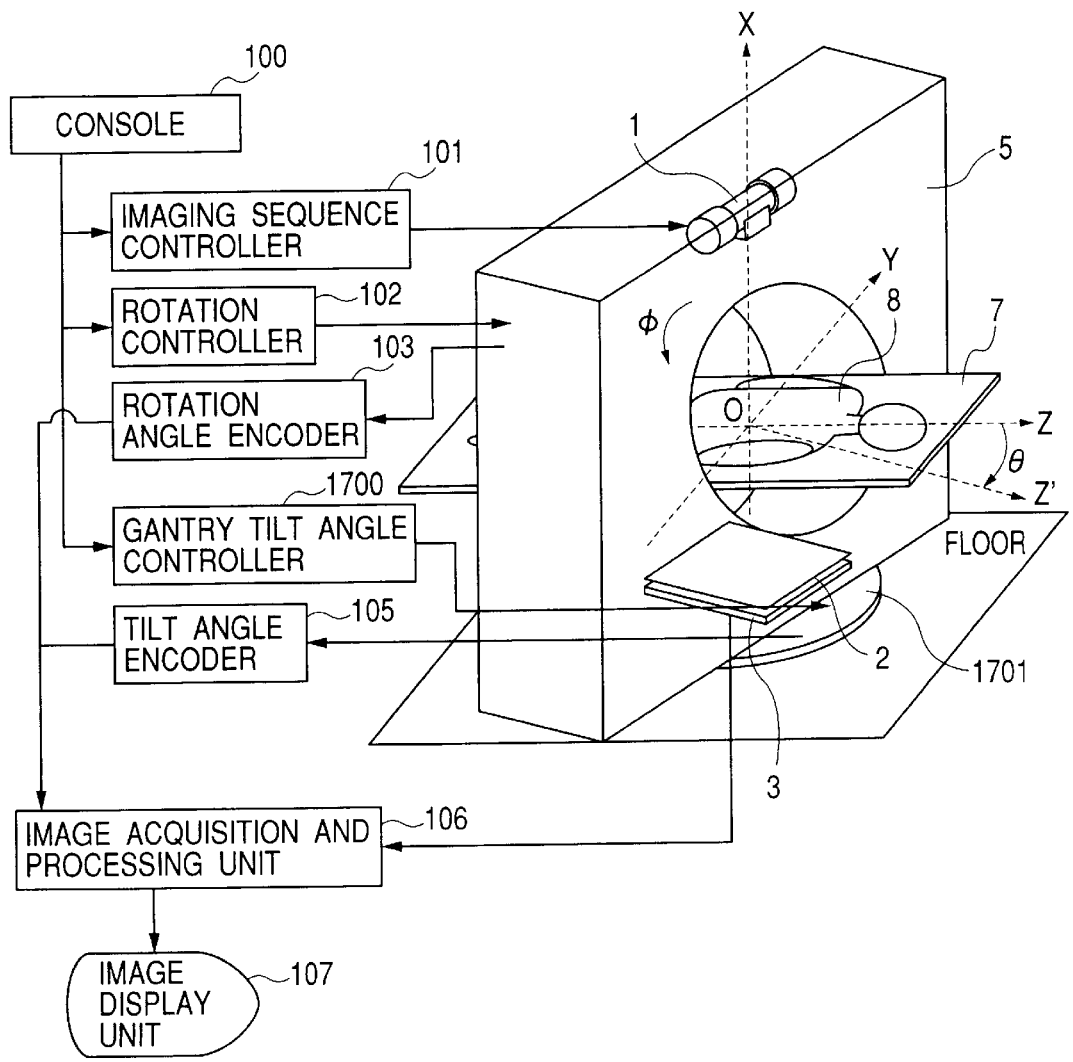
FIG. 17 is a diagram for explaining a schematic configuration of an x-ray CT apparatus according to a second embodiment of the invention.

FIG. 17 is a diagram showing a schematic configuration of an x-ray CT apparatus according to a second embodiment of the invention. The x-ray CT apparatus according to the second embodiment intends to obtain effects similar to those of the x-ray CT apparatus of the first embodiment. In the second embodiment, therefore, the configurations of a gantry rotation stand 1701 and a gantry-tilt angle controller 1701 different from those in the x-ray CT apparatus of the first embodiment will be described in detail. A coordinate system (X, Y, Z) shown in FIG. 17 uses the center O of rotation of the scanning system as the origin and is fixed to the object 8 in a manner similar to the first embodiment. In the second embodiment, the X axis denotes the vertical direction, Y axis denotes the horizontal direction, and X axis indicates the body axis direction. As shown in FIG. 17, one side of a not-illustrated rotating mechanism in the gantry rotation stand 1701 is mounted on the floor. The other side of the rotating mechanism in the gantry rotation stand 1701 is fixed to the gantry 5. The central axis of rotation of the gantry rotation stand 1701 is set on the X axis. That is, the gantry 5 is placed on the gantry rotation stand 1701 so that the center O of rotation of the scanning system exists on the X axis. An amount of deviation between the rotation central axis of the gantry rotation stand 1701 and the center O of rotation of the scanning system is equal to an amount of one pixel of the 2D detector 3 or less in a manner similar to the first embodiment. Like the first embodiment, the gantry rotation stand 1701 outputs a rotational angle of a rotating mechanism, that is, the rotation central axis (Z' axis in FIG. 17) of the scanning system and a tilt angle θ from the Z axis to the tilt angle encoder 105. In the gantry rotation stand 1701, when the angle formed between the Z axis and the Z' axis is zero, the tilt angle θ is set as zero. The clockwise direction seen from the X axis direction of the gantry rotation stand 1701 is the positive direction and the counterclockwise direction is the negative direction. Further, the gantry rotation stand 1701 can be rotated in the direction of θ in the range ±π/9 (=±20°) with respect to the Z axis.

The gantry tilt angle controller 1700 controls the rotation (tilt) of the gantry rotation stand 1701 and a tilting sequence of the gantry 5. The rotation control in the second embodiment is a control performed step by step by using a stepping motor or the like provided for the rotating mechanism. In a manner similar to the first embodiment, obviously, the gantry tilt angle controller 1700 can continuously change the tilt angle θ of the gantry rotation stand 1701.

Referring to FIG. 17, the operation of the x-ray CT apparatus of the second embodiment will be described. By performing controls (for example, controls expressed by Equation 1 and Equations 8 to 16) similar to those in the first embodiment on the tilt angle θ of the gantry 5 and the rotational angle φ of the scanning system, effects similar to those of the first embodiment can be obtained. The initial position in which the rotational angle φ is 0 of the x-ray CT apparatus of the second embodiment is a position in which the x-ray tube position becomes in the Y axis direction. In a manner similar to the x-ray apparatus of the first embodiment, x-rays generated from the x-ray tube 1 pass through the object 8, scattered x-rays are removed by the anti-scattering grid 2 and resultant rays are converted to a digital image by the 2D detector 3. Like in the x-ray CT apparatus of the first embodiment, in the x-ray CT apparatus of the second embodiment, in association with the rotation of the scanning system, the gantry tilt angle controller 1700 controls a known rotating mechanism (not shown) of the gantry rotation stand 1701 to rotate the gantry 5 by using the X axis as a rotation axis. The image acquisition and processing unit 106 once stores output images acquired (measured) by the 2D detector 3 over a 360 degree angular range together with positional information (φ, θ) of the x-ray tube 1 into a not-illustrated memory, reads the output images from the memory, and reconstructs a 3D CT image. The image display unit 107 displays the reconstructed 3D CT image. Since the operation of reconstructing a 3D CT image by the image acquisition and processing unit 106 is similar to that in the x-ray CT apparatus of the first embodiment, its detailed description will not be given. At the time of a scan, the bed 7 and the object 8 are fixed to the floor.

As described above, in the x-ray CT apparatus of the second embodiment, the gantry 5 housing the scanning system fixed to the rotary plate 4 can be tilted in the rotation direction on the gantry rotation stand 1701. At the time of a scan, by tilting the gantry 5 while rotating the scanning system, a helical orbit of the x-ray source can be formed around the object. That is, complete data satisfying the Tuy's condition can be measured, and the same effects as those of the x-ray CT apparatus of the first embodiment can be obtained.

THIRD EMBODIMENT

Figure 18:
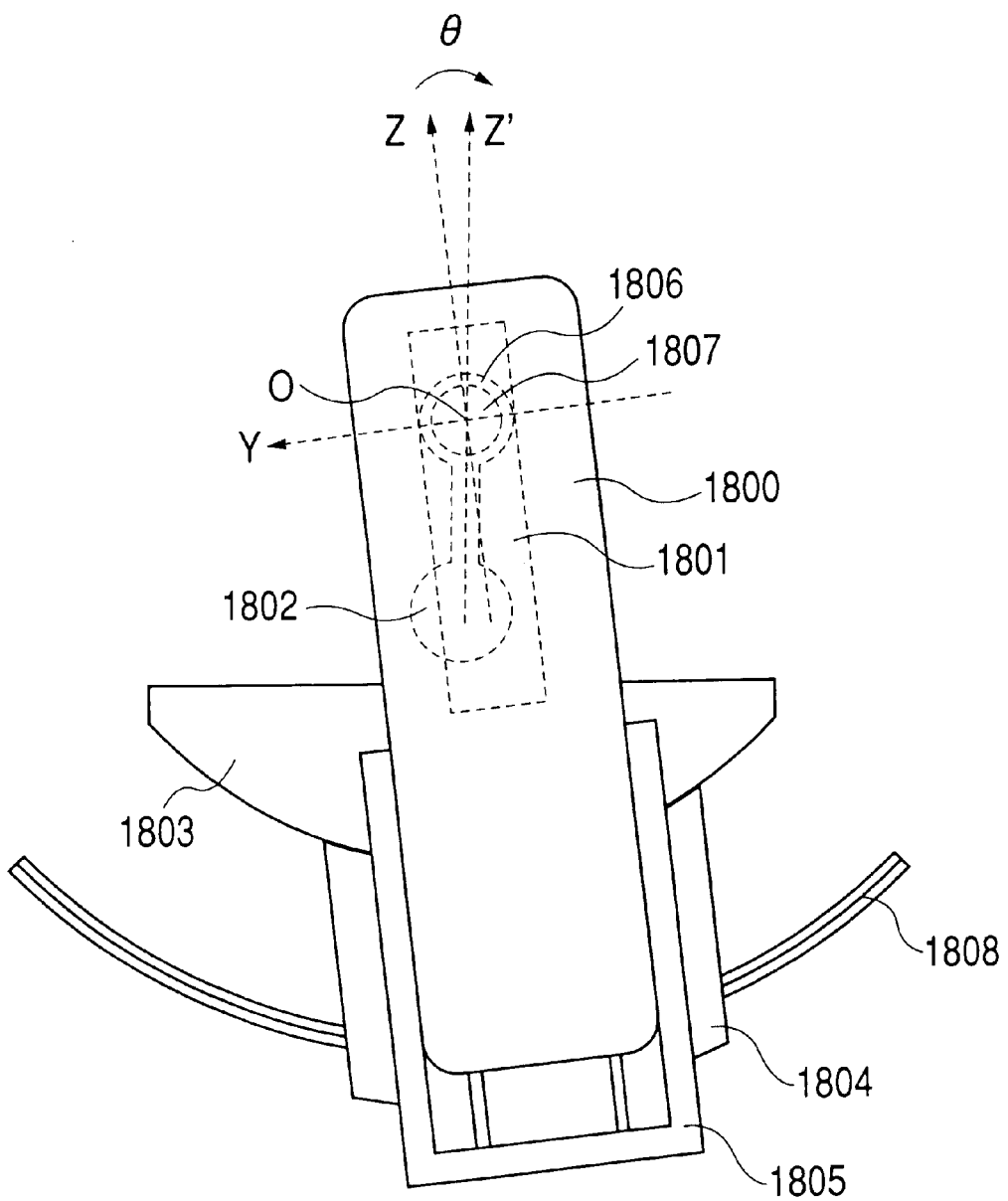
FIG. 18 is a top view for explaining a schematic configuration of an x-ray CT apparatus according to a third embodiment of the invention.
Figure 19:
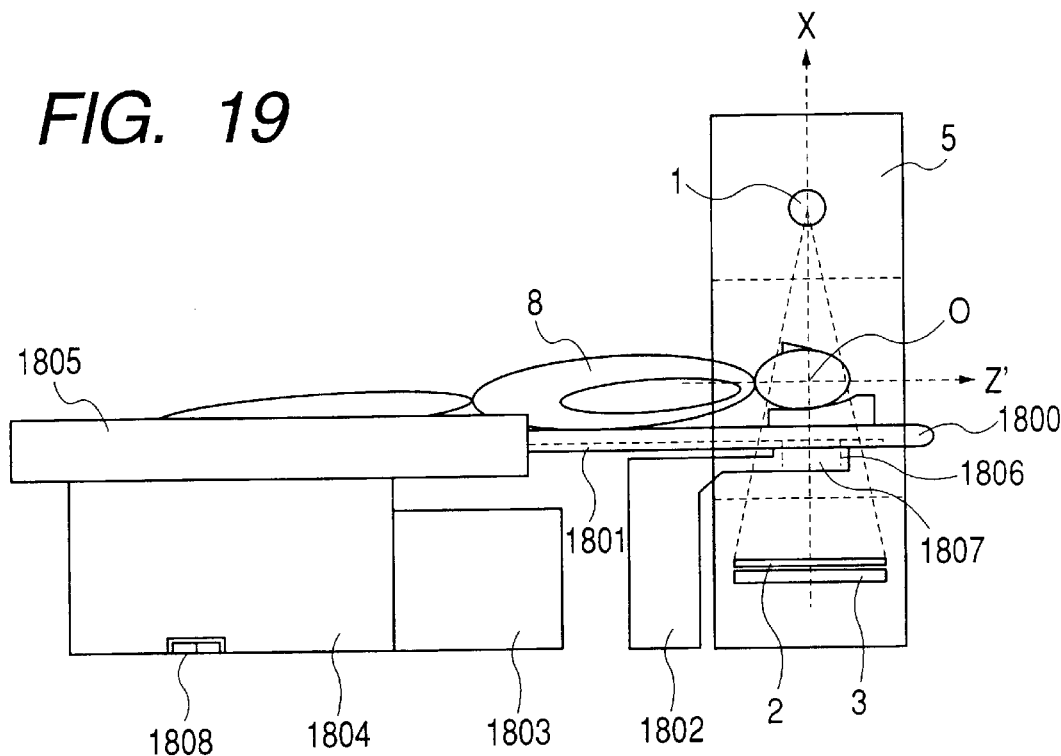
FIG. 19 is a side view for explaining a schematic configuration of the x-ray CT apparatus according to the third embodiment of the invention.

FIG. 18 is a top view for explaining a schematic configuration of an x-ray CT apparatus according to a third embodiment of the invention. FIG. 19 is a side view for explaining the schematic configuration of the x-ray CT apparatus according to the third embodiment of the invention. In the x-ray CT apparatus according to the second embodiment, the whole gantry 5 is rotated around the X axis as a center. In the x-ray CT apparatus of the third embodiment, the gantry 5 is fixed to the floor and the object 8 is rotated around the X axis as a center. In other words, by moving the object 8 in the YZ plane parallel to the floor, effects similar to those of the second embodiment are produced. The coordinate system (X, Y, Z) is fixed to a bed 1805, a horizontal axis parallel to a longitudinal direction of a bed top plate 1800 and passing the center O of rotation is the Z axis, and an axis in the horizontal direction orthogonal to the Z axis is a Y axis. In FIGS. 18 and 19, the gantry 5 is fixed to the floor, and the scanning system rotates around the Z' axis as a rotation axis. In a manner similar to the x-ray CT apparatus of the second embodiment, in the x-ray CT apparatus of the third embodiment, the rotational angle with respect to the Y axis direction of the x-ray tube 1 is set as φ. The Y axis is an axis passing the center O of rotation of the scanning system and in the horizontal direction to the floor. One end of a column 1802 is fixed to the floor and the other end supports a cylindrical column 1806. The central axis of the cylinder of the cylindrical column 1806 is the same as the X axis. To suppress absorption of x-rays, the cylindrical column 1806 is made of a material such as carbon which does not absorb x-rays so much. The cylindrical column 1806 has the center portion 1807 which is hollowed. The top of the cylindrical column 1806 is inserted in a groove 1801 formed on the back face of the bed top plate 1800. The groove 1801 is formed long in the longitudinal direction of the bed top plate 1800.

The bed top plate 1800 is slidable along the bed 1805 in the Z axis direction and a direction opposite to the Z axis direction. A tester can therefore slide the bed top plate 1800 in the Z direction so that a region of interest of the object 8 is set around the rotation center O. On the other hand, the bed top plate 1800 is fixed in the Y direction. The bed 1805 is disposed on a movable stand 1804. The movable stand 1804 moves along a rail 1808 along a fixed stand 1803 fixed to the floor. The rail 1808 is formed in a circular shape around the rotation center O as a center. The movable stand 1804, bed 1805, and bed top plate 1800 can rotate around the rotation center O as a center. The angle formed between the rotation axes Z' and Z of the scanning system is a tilt angle θ. The bed top plate 1800 can be rotated in a range ±π/9 (=±20°) at the maximum in the direction of θ shown by the arrow in the drawing. By performing controls similar to those in the first embodiment on the tilt angle θ and the rotation angle φ (for example, controls expressed by Equation 1 and Equations 8 to 16), effects similar to those of the first and second embodiments can be obtained.

Figure 20:
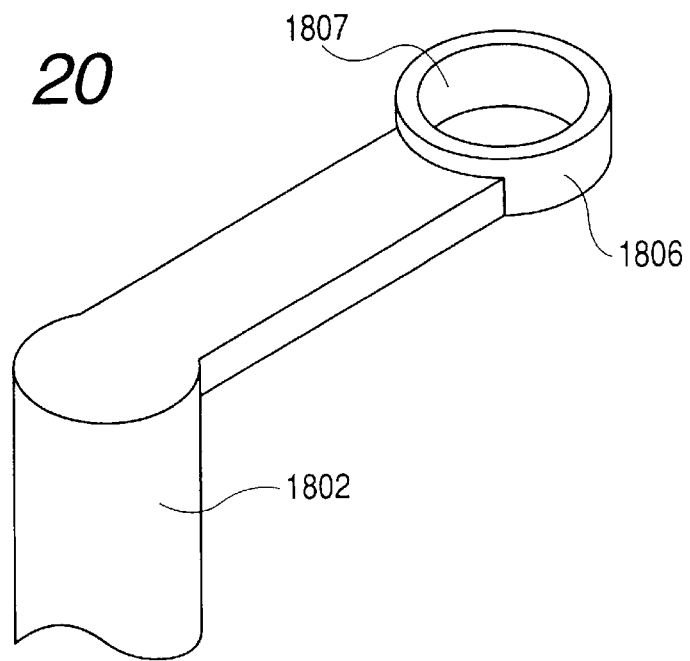
FIG. 20 is a diagram for explaining a schematic configuration of a cylindrical column and a column of the third embodiment.
Figure 21:
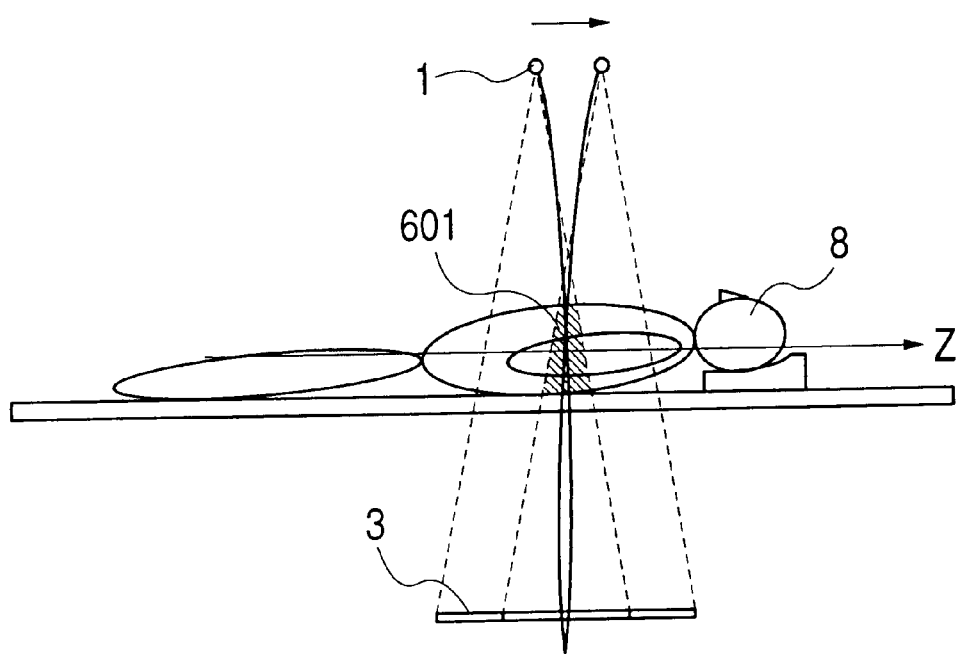
FIG. 21 is a diagram for explaining the positional relation between the x-ray tube and the object in a conventional x-ray CT apparatus.
Figure 22A:
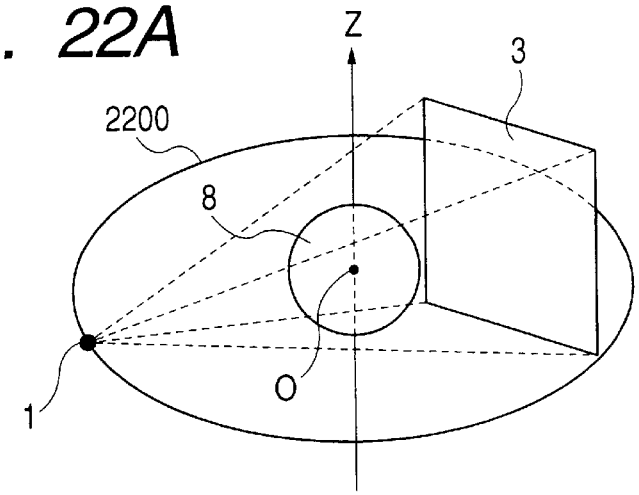
FIGS. 22A, 22B, and 22C are diagrams for explaining a scanning operation in a conventional x-ray CT apparatus.
Figure 22B:
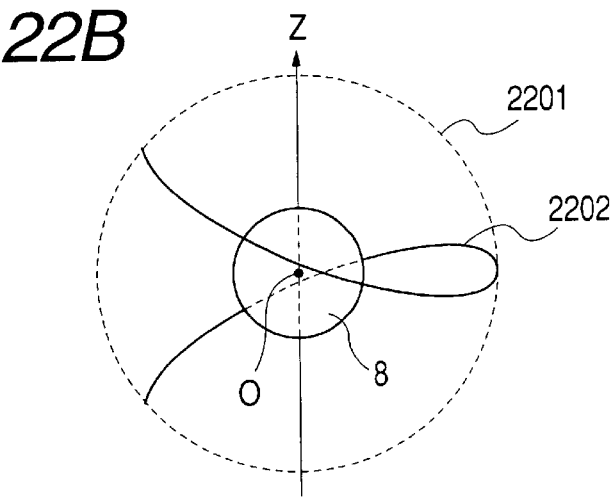
Figure 22C:
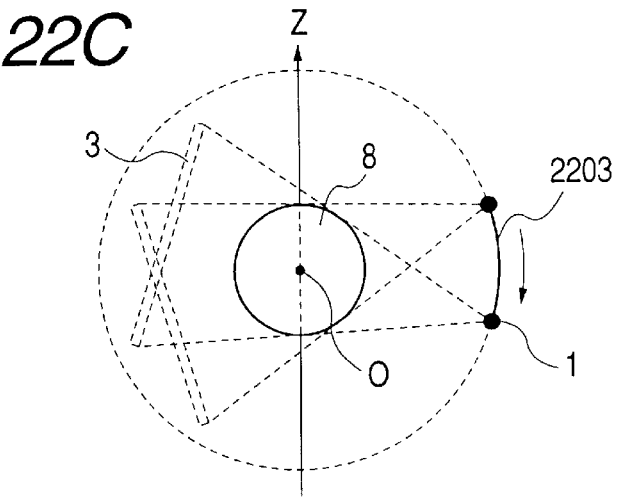

FIG. 20 is a diagram for explaining a schematic configuration of the cylindrical column and column of the third embodiment. As obvious from FIG. 20, in the x-ray CT apparatus of the third embodiment, when the column 1802 is provided in the rotation center of the bed 1805, the column 1802 becomes an obstacle and the scanning system cannot be rotated around the object 8. In the x-ray CT apparatus of the third embodiment, therefore, the portion from the column 1802 to the cylindrical column 1806 is formed in an L shape. In the x-ray CT apparatus of the third embodiment, by forming a cylindrical shape having a hollow in the X axis direction in a portion of the rotation center O of the cylindrical column 1806, an x-ray absorption amount of the cylindrical column 1806 is minimized. In the third embodiment, the central axis of the cylindrical portion 1807 of the cylindrical column 1806 coincides with the rotation center O of the scanning system.

As described above, in the x-ray CT apparatus of the third embodiment, the bed 1805 and the bed top plate 1800 can be tilted around the central axis of the cylindrical column 1806 extending from the column 1802. Since the rotation axis of the scanning system and the tilt angle θ with respect to the object 8 can be changed, effects similar to those of the second embodiment can be produced.

As understood from the above description, according to the first to third embodiments, while fixing the center of the view field of the 2D detector to a point indicated by the rotation center O, a cone-beam CT scan in a helical orbit of the x-ray source (helical scan) can be executed. Therefore, complete data necessary to reconstruct an image of the object can be collected without reducing the field of view. Since the helical scan can be executed in a state where the object is stationary, a human body or the like can be scanned.

In the x-ray CT apparatuses of the first to third embodiments, the range of the tilt angle θ as an angle formed between the rotation central axis of the rotary plate 4 and the Z axis set to the object 8 is ±π/9 (=±20°). The invention is not limited to the range. Obviously, as long as the open end of the gantry 5 and the object 8 or bed top plate 7 do not come into contact with each other, the range of the tilt angle can be set to ±π/9 (=±20°) or larger. In the x-ray CT apparatuses of the first to third embodiments, either the gantry 5 or the object 8 is moved. Obviously, also in the case where the tilting mechanism of the gantry 5 of the first and second embodiments and the object tilting mechanism of the third embodiment are combined, effects similar to those described in the first to third embodiments can be obtained. Apparently, the tilting mechanisms of the gantry 5 of the first and second embodiments are combined and the gantry 5 may be tilted three-dimensionally. In the x-ray CT apparatuses of the first to third embodiments, the 2D detector 3 disclosed in Literature 5 is used as an x-ray detector. Needless to say, when a conventional x-ray detector including an x-ray image intensifier and a television camera or the like is used in place of the 2D detector 3, the same effects as those of the first to third embodiments can be obtained. Although the initial position of the x-ray tube 1 is in the direction of the central axis of tilting of the gantry 5 in the first to third embodiments, the direction is not limited to the direction but may be other directions. Although the scanning system is tilted with the gantry 5 in the x-ray CT apparatuses in the first to third embodiments, the invention is not limited to the configuration. Obviously, it is also possible to fix the gantry 5 to the floor and tilt the scanning system by tilting only the rotary plate 4. By fixing the gantry 5, the movable portion can be prevented from being exposed.

Although the invention has been concretely described above on the basis of the embodiments of the invention, obviously, the invention is not limited to the foregoing embodiments but can be variously modified within the range not departing from its gist.

The reference numerals used for explaining the drawings denote as follows.

1 . . . x-ray tube, 2 . . . anti-scattering grid, 3 . . . two-dimensional detector, 4 . . . rotary plate (scanner), 5 . . . gantry, 6 . . . supporting stand, 7 . . . bed, 8 . . . object, 9 . . . frame memory, 10 . . . memory, 100 . . . console, 101 . . . imaging sequence controller, 102 . . . rotation controller, 103 . . . rotational angle encoder, 104 . . . gantry-tilt angle controller, 105 . . . tilt angle encoder, 106 . . . image acquisition and processing unit, 107 . . . image display unit, 1700 . . . gantry-tilt angle controller, 1701 . . . gantry rotation stand, 601 . . . common region, 602 . . . spherical shell, 603, 1101, 1301 to 1307 . . . orbits of x-ray tube, 1100 . . . imaginary detector, 1700 . . . gantry rotating means, 1701 . . . gantry rotation stand, 1800 . . . bed top plate, 1801 . . . groove, 1802 . . . column, 1803 . . . bed top plate, 1804 . . . movable stand, 1805 . . . bed, 1806 . . . cylindrical column, 1807 . . . center portion of cylindrical column, 1808 . . . rail.

Industrial Applicability

An x-ray CT apparatus according to the invention can be effectively used as a medical diagnostic system.

What is claimed is:

1. An x-ray CT apparatus comprising:
a scanner on which a scanning system is mounted, the scanning system having an x-ray source for generating radial x-rays to be irradiated to an object and image acquiring means provided so as to face said x-ray source and acquiring projection images of said object;
rotating means for rotating said scanner around said object;
tilting means for changing a tilt angle formed between a surface of rotation of said scanner and a body axis of said object;
means for generating a CT image of said object from said projections images acquired from a plurality of directions while simultaneously rotating said scanner and changing said tilt angle; and
display means for displaying said CT image;
wherein said tilting means synchronizes a period of rotation of (360°×N) (where, N denotes a natural number) of said scanner by said rotating means with a period from a start until an end of the change of said tilt angle by said tilting means.

2. An x-ray CT apparatus comprising:
a scanner on which a scanning system is mounted, the scanning system having an x-ray source for generating radial x-rays to be irradiated to an object and image acquiring means provided so as to face said x-ray source and acquiring projection images of said object;
rotating means for rotating said scanner around said object;
tilting means for changing a tilt angle formed between a surface of rotation of said scanner and a body axis of said object;
means for generating a CT image of said object from said projections images acquired from a plurality of directions while simultaneously rotating said scanner and changing said tilt angle; and display means for displaying said CT image;

wherein said tilting means synchronizes the period of rotation of (360°×I+α) (where, I denotes a natural number and α denotes an arbitrary angle in a range of 0°<α<360°) of said scanner by said rotating means with a period from a start until an end of the change of said tilt angle by said tilting means.

3. An x-ray CT imaging method comprising:

a step of rotating a scanner on which a scanning system is mounted around an object, the scanning system having an x-ray source for generating radial x-rays to be irradiated to said object and image acquiring means provided so as to face said x-ray source and acquiring projection images of said object;

a tilting step of tilting a surface of rotation of said scanner to change a tilt angle formed between the surface of rotation of said scanner and a body axis of said object;

an image acquiring step of acquiring projection images of said object by using the x-rays transmitted through said object;

an image reproducing step of generating a CT image of said object from said projection images acquired from a plurality of directions while simultaneously rotating said scanner and changing said tilt angle; and a display step of displaying said CT image of said object, wherein a period of rotation of (360°×I+α) (where, I denotes a natural number and α denotes an arbitrary angle in a range of 0°≦α<360°) of said scanner and a period from a start until an end of the change of said tilt angle are synchronized with each other.

4. The x-ray CT imaging method according to claim 3, further comprising a stopping step of temporarily stopping the change in said tilt angle during said rotating step.

5. The x-ray CT imaging method according to claim 3, wherein, in said tilting step, said tilt angle is changed so that an upper part of a gantry housing said scanner is moved away from a head of said object.

6. An x-ray CT apparatus comprising:

an x-ray source for generating x-rays to be irradiated to an object;

an x-ray detector for detecting x-rays transmitted through said object;

a scanner for scanning said object with the x-rays irradiated to said object, said scanner supporting said x-ray source and said x-ray detector so as to face each other and being provided with a rotating mechanism for rotating said x-ray source and said x-ray detector around said object;

a tilting mechanism for changing a tilt angle formed between the surface of rotation of said scanner and a body axis of said object, in a predetermined tilt angle range;

a bed for supporting said object in a position between said x-ray source and said x-ray detector;

control means for controlling the generation of the x-rays by said x-ray source, the detection of the transmitted x-rays by said x-ray detector, the rotation angle by said rotating mechanism and the tilt angle by said tilting mechanism so as to simultaneously carry out the rotation operation of said scanner and the tilting operation of changing the tilt angle by said tilting mechanism; and image reconstruction means for reconstructing a 3D CT image of said object by using the detection signal of the transmitted x-rays by said x-ray detector;

wherein said tilting mechanism holds a constant change amount of said tilt angle with respect to a unit rotation amount of said scanner; and wherein said tilting mechanism synchronizes a period of rotation of (360°×N) (where, N denotes a natural number) of said scanner by said rotating mechanism with a period from a start until an end of the change of said tilt angle by said tilting mechanism.

7. The x-ray CT apparatus according to claim 6, wherein said predetermined tilt angle range is set within a range from −20° to +20°.

8. An x-ray CT apparatus comprising:

an x-ray source for generating x-rays to be irradiated to an object;

an x-ray detector for detecting x-rays transmitted through said object;

a scanner for scanning said object with the x-rays irradiated to said object, said scanner supporting said x-ray source and said x-ray detector so as to face each other and being provided with a rotating mechanism for rotating said x-ray source and said x-ray detector around said object;

a tilting mechanism for changing a tilt angle formed between the surface of rotation of said scanner and a body axis of said object, in a predetermined tilt angle range;

a bed for supporting said object in a position between said x-ray source and said x-ray detector;

control means for controlling the generation of the x-rays by said x-ray source, the detection of the transmitted x-rays by said x-ray detector, the rotation angle by said rotating mechanism and the tilt angle by said tilting mechanism so as to simultaneously carry out the rotation operation of said scanner and the tilting operation of changing the tilt angle by said tilting mechanism; and image reconstruction means for reconstructing a 3D CT image of said object by using the detection signal of the transmitted x-rays by said x-ray detector;

wherein said tilting mechanism holds a constant change amount of said tilt angle with respect to a unit rotation amount of said scanner; and wherein said tilting mechanism synchronizes a period of rotation of (360°×I+α) (where, I denotes a natural number and a denotes an arbitrary angle in a range of 0°<α<360°) of said scanner by said rotating mechanism with a period from a start until an end of the change of said tilt angle by said tilting mechanism.

9. An x-ray CT apparatus comprising:

a scanner on which a scanning system is mounted, the scanning system having an x-ray source for emitting radial x-rays to be irradiated to an object and image acquiring means provided so as to face said x-ray source and acquiring projection images of said object by using the x-rays transmitted through said object;

rotating means for rotating said scanner around said object;

tilting means for changing a tilt angle formed between a surface of rotation of said scanner and a body axis of said object;

means for controlling operations of said rotating means and said tilting means so that the rotating of said scanner and the changing of said tilt angle are simultaneously carried out; and means for generating a CT image of said object from said projection images acquired from a plurality of directions while simultaneously rotating said scanner and changing said tilt angle; and display means for displaying said CT image;

wherein said tilting means holds a constant change amount of said tilt angle with respect to a unit rotation amount of said scanner; and wherein said tilting means synchronizes a period of the rotation of (360°×N) (where, N denotes a natural number) of said scanner by said rotating means with a period from a start until an end of the change of said tilt angle by said tilting means.

10. An x-ray CT apparatus comprising:

a scanner on which a scanning system is mounted, the scanning system having an x-ray source for emitting radial x-rays to be irradiated to an object and image acquiring means provided so as to face said x-ray source and acquiring projection images of said object by using the x-rays transmitted through said object;

rotating means for rotating said scanner around said object;

tilting means for changing a tilt angle formed between a surface of rotation of said scanner and a body axis of said object;

means for controlling operations of said rotating means and said tilting means so that the rotating of said scanner and the changing of said tilt angle are simultaneously carried out; and means for generating a CT image of said object from said projection images acquired from a plurality of directions while simultaneously rotating said scanner and changing said tilt angle; and display means for displaying said CT image;

wherein said tilting means holds a constant change amount of said tilt angle with respect to a unit rotation amount of said scanner; and wherein said tilting means synchronizes a period of the rotation of (360°×I+α) (where, I denotes a natural number and α denotes an arbitrary angle in a range of 0°<α<360°) of said scanner by said rotating means with a period from a start until an end of the change of said tilt angle by said tilting means.

11. An x-ray CT imaging method comprising the steps of:

rotating a scanner on which a scanning system is mounted around an object, the scanning system having an x-ray source for generating radial x-rays to be irradiated onto said object and image acquiring means provided so as to face said x-ray source and acquiring projection images of said object, and tilting the surface of the rotation of said scanner to change the tilt angle formed between the surface of the rotation of said scanner and a body axis of said object, wherein the rotation of said scanner and the changing of the tilt angle are simultaneously carried out;

acquiring projection images from a plurality of directions of said object by using the x-rays transmitted through said object; and, reproducing a CT image of said object from said projection images while simultaneously rotating said scanner and changing said tilt angle; and displaying said CT image of said object;

wherein the period of the rotation of (360°×I+α) (where, I denotes a natural number and α denotes an arbitrary angle in a range of 0°<α<360°) of said scanner and a period from a start until an end of the change of said tilt angle are synchronized.

* * * * *